US006695851B2

(12) United States Patent
Zdeblick et al.

(10) Patent No.: US 6,695,851 B2
(45) Date of Patent: Feb. 24, 2004

(54) METHODS AND INSTRUMENTS FOR INTERBODY FUSION

(75) Inventors: Thomas Zdeblick, Middleton, WI (US); Thomas McGahan, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/213,864

(22) Filed: Aug. 7, 2002

(65) Prior Publication Data

US 2002/0193802 A1 Dec. 19, 2002

Related U.S. Application Data

(60) Division of application No. 09/781,589, filed on Feb. 5, 2001, now Pat. No. 6,471,724, which is a division of application No. 09/014,901, filed on Jan. 28, 1998, now Pat. No. 6,206,922, which is a continuation-in-part of application No. 08/604,874, filed on Feb. 22, 1996, now abandoned, which is a continuation-in-part of application No. 08/411,017, filed on Mar. 27, 1995, now Pat. No. 5,782,919.

(51) Int. Cl.[7] ............................. A61B 17/58; A61F 2/44
(52) U.S. Cl. ...................................... 606/96; 623/17.11
(58) Field of Search ................. 623/17.11, 17.12–17.16; 606/61, 99, 90, 96, 60, 72, 73, 74, 80, 86–88

(56) References Cited

U.S. PATENT DOCUMENTS

| 3,486,505 A | 12/1969 | Morrison | 128/303 |
|---|---|---|---|
| 3,848,601 A | 11/1974 | Ma et al. | |
| 4,309,777 A | 1/1982 | Patil | 3/1.91 |
| 4,349,921 A | 9/1982 | Kuntz | |
| 4,501,269 A | 2/1985 | Bagby | |
| 4,526,909 A | 7/1985 | Urist | 523/115 |
| 4,545,374 A | 10/1985 | Jacobson | 128/303 |
| 4,573,448 A | 3/1986 | Kambin | 128/1 |
| 4,596,574 A | 6/1986 | Urist | 623/16 |
| 4,599,086 A | 7/1986 | Doty | 623/17 |

(List continued on next page.)

FOREIGN PATENT DOCUMENTS

| CA | 2015507 | 4/1990 | A61F/2/44 |
|---|---|---|---|
| DE | 3505567 A | 6/1986 | A61F/2/28 |
| DE | 4302397 A1 | 1/1992 | A61F/2/44 |
| EP | 0077159 | 10/1982 | A61B/17/00 |
| EP | 0179695 | 9/1985 | A61F/2/44 |

(List continued on next page.)

OTHER PUBLICATIONS

*Laparoscopic Bone Dowel Surgical Technique*, by Sofamor Danek USA, 1800 Pyramid Place, Memphis, TN 38132, Lit LBD ST95 Copyright 1995 Sofamor Danek.

Primary Examiner—Corrine McDermott
Assistant Examiner—Alvin Stewart
(74) Attorney, Agent, or Firm—Woodard, Emhardt, Moriarty, McNett & Henry LLP

(57) ABSTRACT

A laparoscopic surgical technique is provided for preparing a site for implantation of a novel fusion device or implant. In accordance with one embodiment of the technique, a laparoscope is provided having an outer sleeve with distraction fingers at one end to distract the disc space. The laparoscope provides a sealed working channel to the disc space, through which the disc space is distracted, the vertebral endplates and surrounding disc is reamed, and the fusion device inserted. A distraction plug is provided for centering the outer sleeve and for providing midline distraction of the disc space. In one embodiment, a fusion device includes diverging bone screws passing through an end wall and upper and lower walls of the device to engage the adjacent vertebrae. In another embodiment, a connector plate is engaged to bilaterally position fusion devices to prevent rotation and resist expulsion of the devices from the disc space.

44 Claims, 19 Drawing Sheets

U.S. PATENT DOCUMENTS

| | | | |
|---|---|---|---|
| 4,678,470 A | 7/1987 | Nashef et al. ................. 623/16 |
| 4,714,469 A | 12/1987 | Kenna ......................... 623/17 |
| 4,736,738 A | 4/1988 | Lipovsek et al. ............. 128/92 |
| 4,743,256 A | 5/1988 | Brantigan |
| 4,743,259 A | 5/1988 | Bolander et al. ............. 623/16 |
| 4,759,766 A | 7/1988 | Buettner-Janz et al. ....... 623/17 |
| 4,772,287 A | 9/1988 | Ray et al. ..................... 623/17 |
| 4,820,305 A | 4/1989 | Harms et al. |
| 4,834,757 A | 5/1989 | Brantigan |
| 4,863,476 A | 9/1989 | Shepperd ..................... 623/17 |
| 4,877,020 A | 10/1989 | Vich |
| 4,878,915 A | 11/1989 | Brantigan |
| 4,892,545 A | 1/1990 | Day et al. ..................... 623/17 |
| 4,904,261 A | 2/1990 | Dove et al. |
| 4,917,704 A | 4/1990 | Frey et al. .................... 623/17 |
| 4,932,975 A | 6/1990 | Main et al. ................... 623/17 |
| 4,936,848 A | 6/1990 | Bagby |
| 4,961,740 A | 10/1990 | Ray et al. |
| 5,002,576 A | 3/1991 | Fuhrmann et al. ............ 623/17 |
| 5,015,247 A | 5/1991 | Michelson |
| 5,020,519 A | 6/1991 | Hayes et al. .................. 128/69 |
| 5,030,474 A | 7/1991 | Saita et al. ..................... 427/2 |
| 5,055,104 A | 10/1991 | Ray ............................. 606/61 |
| 5,062,850 A | 11/1991 | MacMillan et al. ........... 623/17 |
| 5,068,122 A | 11/1991 | Kokubo et al. ................. 427/2 |
| 5,071,437 A | 12/1991 | Steffee ......................... 623/17 |
| 5,092,893 A | 3/1992 | Smith ........................... 623/17 |
| 5,108,395 A | 4/1992 | Laurain ........................ 606/61 |
| 5,128,169 A | 7/1992 | Saita et al. ..................... 427/2 |
| RE34,037 E | 8/1992 | Inoue et al. ................... 604/93 |
| 5,147,402 A | 9/1992 | Bohler et al. ................. 623/16 |
| 5,147,404 A | 9/1992 | Downey ....................... 623/17 |
| 5,164,187 A | 11/1992 | Constantz et al. .......... 424/423 |
| 5,188,670 A | 2/1993 | Constantz ................... 118/667 |
| 5,192,327 A | 3/1993 | Brantigan |
| 5,236,456 A | 8/1993 | O'Leary et al. ............... 623/16 |
| 5,236,460 A | 8/1993 | Berber ......................... 623/17 |
| 5,279,831 A | 1/1994 | Constantz et al. .......... 424/423 |
| 5,282,861 A | 2/1994 | Kaplan |
| 5,290,312 A | 3/1994 | Kojimoto et al. |
| 5,306,307 A | 4/1994 | Senter et al. ................. 623/17 |
| 5,306,309 A | 4/1994 | Wagner et al. ................ 623/17 |
| 5,306,310 A | 4/1994 | Siebels ........................ 623/17 |
| 5,330,826 A | 7/1994 | Taylor et al. ............... 428/216 |
| 5,338,433 A | 8/1994 | Maybee et al. ............. 205/178 |
| 5,344,654 A | 9/1994 | Rueger et al. .............. 424/423 |
| 5,348,026 A | 9/1994 | Davidson ................... 128/898 |
| 5,360,430 A | 11/1994 | Lin .............................. 606/61 |
| 5,397,364 A | 3/1995 | Kozak et al. ................. 623/17 |
| 5,405,391 A | 4/1995 | Hednerson et al. |
| 5,417,975 A | 5/1995 | Lussi et al. ................. 424/423 |
| 5,423,816 A | 6/1995 | Lin .............................. 606/61 |
| 5,423,817 A | 6/1995 | Lin .............................. 606/61 |
| 5,425,769 A | 6/1995 | Snyders, Jr. .................. 623/16 |
| 5,425,772 A | 6/1995 | Brantigan ..................... 623/17 |
| 5,431,658 A | 7/1995 | Moskovich ................... 606/99 |
| 5,439,464 A | 8/1995 | Shapiro ........................ 606/83 |
| 5,439,684 A | 8/1995 | Prewett et al. .............. 424/422 |
| 5,443,514 A | 8/1995 | Steffee |
| 5,443,515 A | 8/1995 | Cohen et al. ................. 623/17 |
| 5,455,231 A | 10/1995 | Constantz et al. ............ 514/21 |
| 5,458,638 A | 10/1995 | Kuslich et al. |
| 5,464,439 A | 11/1995 | Gendler ....................... 623/16 |
| 5,484,437 A | 1/1996 | Michelson |
| 5,489,307 A | 2/1996 | Kuslich et al. ............... 623/17 |
| 5,489,308 A | 2/1996 | Kuslich et al. ............... 623/17 |
| 5,507,813 A | 4/1996 | Dowd et al. .................. 623/16 |
| 5,510,396 A | 4/1996 | Prewett et al. .............. 523/113 |
| 5,514,180 A | 5/1996 | Heggeness et al. ........... 623/17 |
| 5,540,688 A | 7/1996 | Navas .......................... 606/61 |
| 5,549,612 A | 8/1996 | Yapp et al. ................... 606/69 |
| 5,562,736 A | 10/1996 | Ray et al. ..................... 623/17 |
| D377,095 S | 12/1996 | Michelson |
| D377,096 S | 12/1996 | Michelson |
| 5,585,116 A | 12/1996 | Boniface et al. ............ 424/549 |
| 5,591,235 A | 1/1997 | Kuslich |
| 5,593,409 A | 1/1997 | Michelson |
| 5,601,556 A | 2/1997 | Pisharodi |
| 5,609,635 A | 3/1997 | Michelson ................... 623/17 |
| 5,609,636 A | 3/1997 | Kohrs et al. |
| 5,645,591 A | 7/1997 | Kuberasampath et al. .... 623/16 |
| 5,645,598 A | 7/1997 | Brosnahan, III ............. 623/17 |
| 5,646,084 A | 7/1997 | Patton et al. ................ 502/152 |
| 5,647,872 A | 7/1997 | Gilbert et al. ................. 606/61 |
| 5,658,285 A | 8/1997 | Marnay et al. ................ 606/61 |
| 5,669,909 A | 9/1997 | Zdeblick et al. .............. 606/61 |
| 5,676,666 A | 10/1997 | Oxland et al. ................ 606/61 |
| 5,681,311 A | 10/1997 | Foley et al. ................... 606/61 |
| 5,683,391 A | 11/1997 | Boyd ........................... 606/61 |
| 5,683,394 A | 11/1997 | Rinner ........................ 606/86 |
| 5,683,463 A | 11/1997 | Godefroy et al. ............. 623/17 |
| 5,697,889 A | 12/1997 | Slotman et al. ............. 600/204 |
| 5,741,253 A * | 4/1998 | Michelson ................... 606/61 |
| 5,766,252 A | 6/1998 | Henry et al. ................. 623/17 |
| 5,766,253 A | 6/1998 | Brosnahan, III ............. 623/17 |
| 5,797,909 A | 8/1998 | Michelson ................... 606/61 |
| 5,888,224 A | 3/1999 | Beckers et al. ............... 623/17 |
| 5,941,880 A | 8/1999 | Errico et al. ................. 606/61 |
| 6,042,582 A * | 3/2000 | Ray ............................. 606/61 |
| 6,066,175 A | 5/2000 | Henderson et al. |
| 6,149,686 A | 11/2000 | Kuslich et al. |
| 6,342,074 B1 | 1/2002 | Simpson |

FOREIGN PATENT DOCUMENTS

| | | | | |
|---|---|---|---|---|
| EP | 0307241 | 3/1989 | ........... A61B/17/58 |
| EP | 0450886 A1 | 3/1991 | ............ A61M/1/00 |
| EP | 0635246 | 1/1995 | ............ A61F/2/44 |
| EP | 0646366 | 5/1995 | ............ A61F/2/44 |
| EP | 0637440 | 8/1995 | ............ A61F/2/44 |
| EP | 0716840 A2 | 12/1995 | ............ A61F/2/44 |
| EP | 0796593 A2 | 3/1997 | ........... A61B/17/16 |
| FR | 2631539 A1 | 5/1988 | ........... A61B/17/56 |
| FR | 2710519 A1 | 9/1993 | ........... A61B/17/70 |
| FR | 2727003 A1 | 11/1994 | ............ A61F/2/44 |
| FR | 2727005 A1 | 11/1994 | ............ A61F/2/44 |
| FR | 2724312 A1 | 4/1995 | ............ A61F/2/44 |
| WO | WO 87/07827 | 12/1987 | ............ A61F/2/44 |
| WO | WO 90/00037 | 1/1990 | ............ A61F/2/44 |
| WO | WO 91/06261 | 5/1991 | ............ A61F/2/44 |
| WO | WO 92/14423 | 9/1992 | ............ A61F/2/44 |
| WO | WO 94/11040 | 5/1994 | .......... A61M/5/178 |
| WO | WO 94/26893 | 11/1994 | .......... C12N/15/12 |
| WO | WO 95/08306 | 3/1995 | ............ A61F/2/44 |
| WO | WO 95/15133 | 6/1995 | ............ A61F/2/44 |
| WO | WO 95/26164 | 10/1995 | ........... A61B/17/70 |
| WO | WO 96/27321 | 2/1996 | |
| WO | WO 96/22747 | 8/1996 | ............ A61F/2/44 |
| WO | WO 96/27345 | 9/1996 | |
| WO | WO 96/40016 | 12/1996 | ............ A61F/2/44 |
| WO | WO 97/20526 | 6/1997 | ............ A61F/2/44 |
| WO | WO 97/30666 | 8/1997 | ............ A61F/2/46 |
| WO | WO 97/31517 | 8/1997 | ........... J16B/37/14 |

* cited by examiner

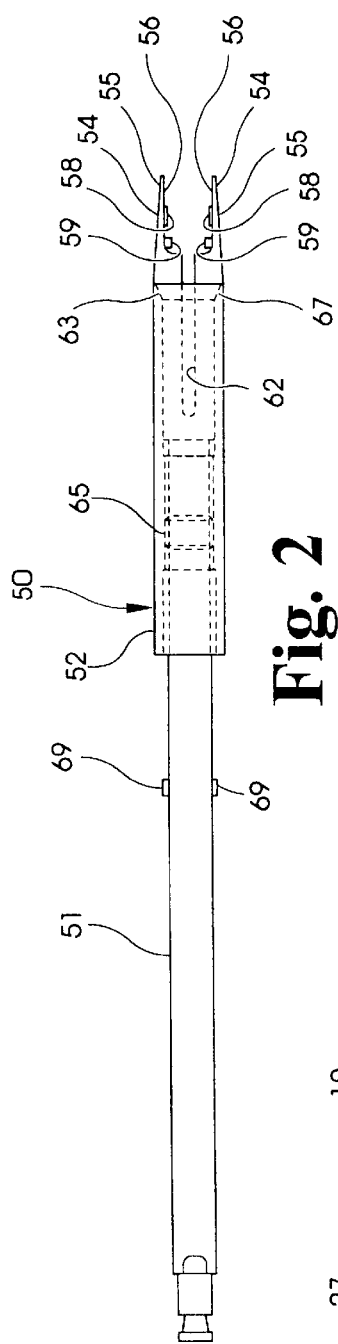
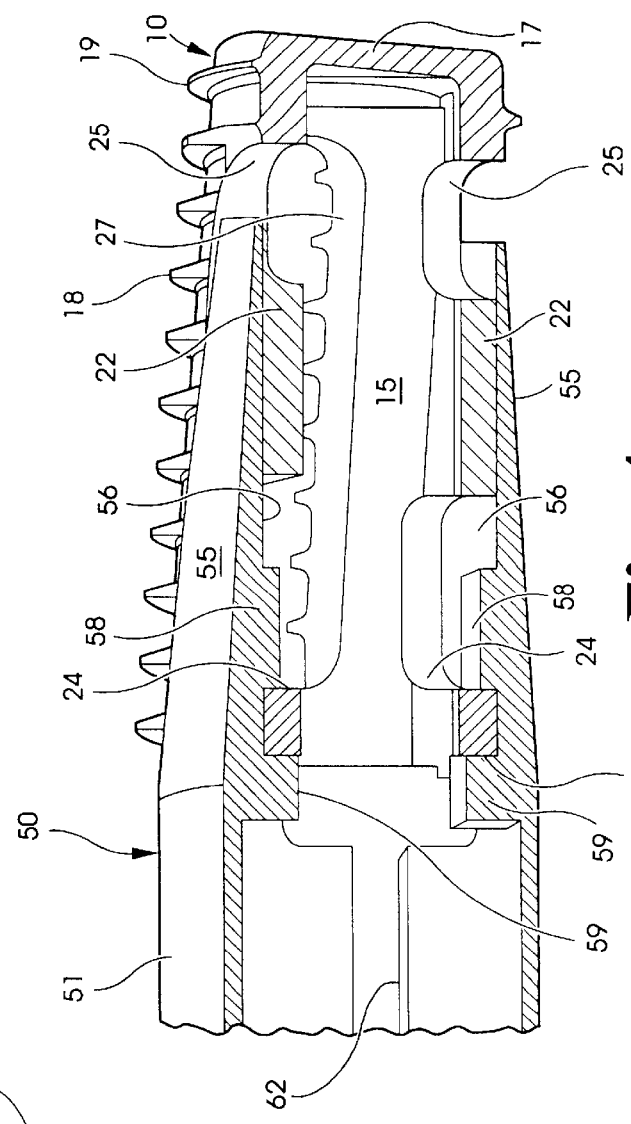
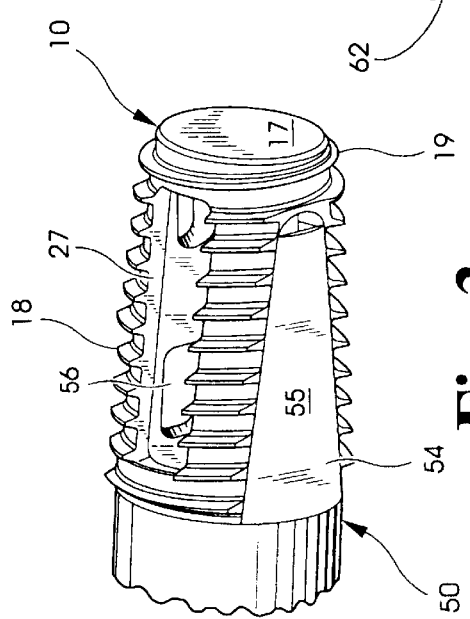

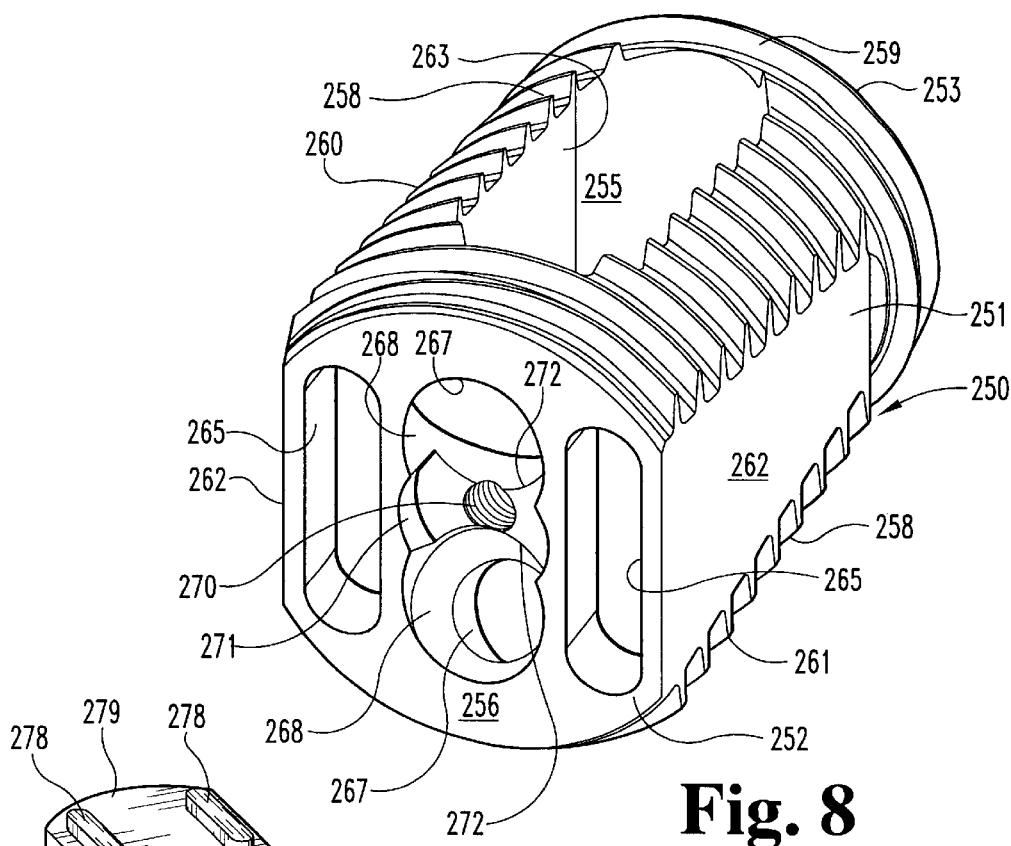
Fig. 8
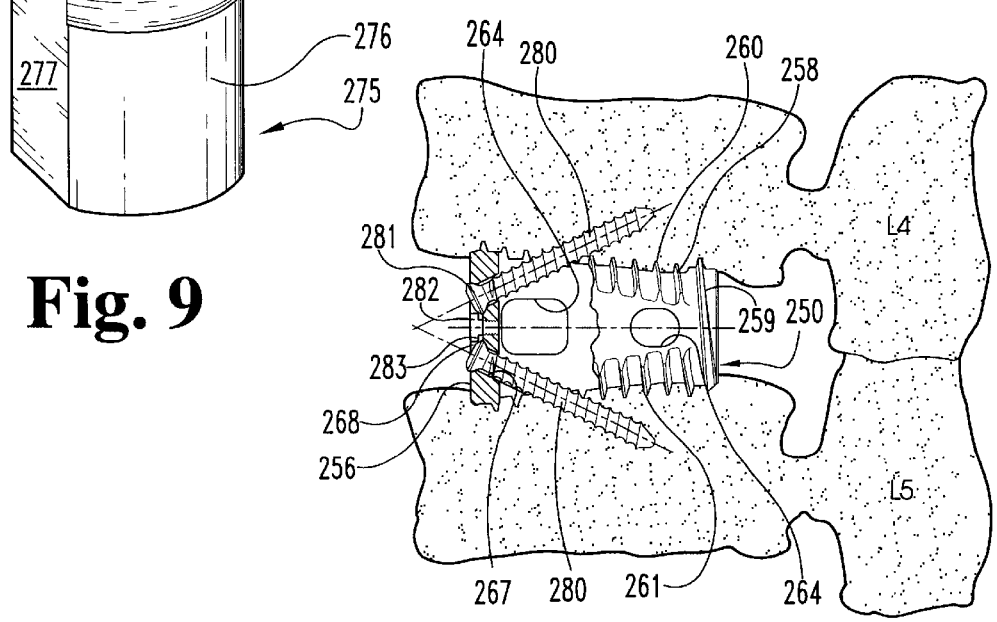
Fig. 9
Fig. 10

1. Dilate the disc space (slight lordosis):

2. Place outer sleeve & drill minor diameter hole:

3. Insert implant to secure lordosis required

4. Remove implant driver

1. Dilate the disc space:

2. Place outer sleeve & drill minor diameter hole:

3. Insert implant to appropriate depth

4. Rotate to restore lordosis, remove implant driver

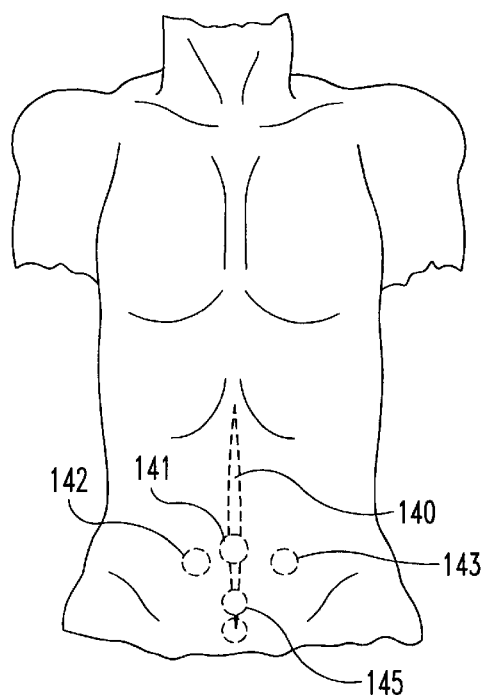
Fig. 13
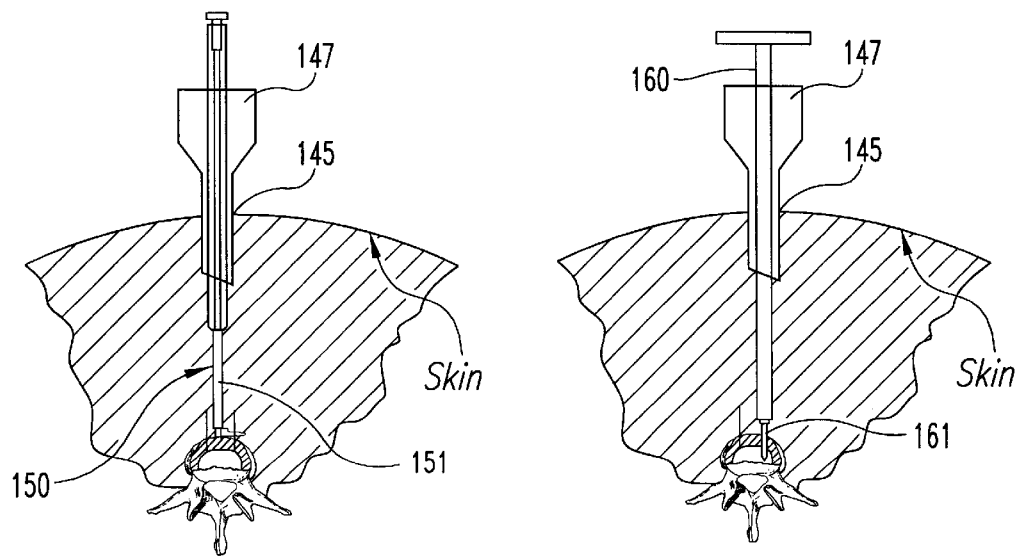
Fig. 14   Fig. 16

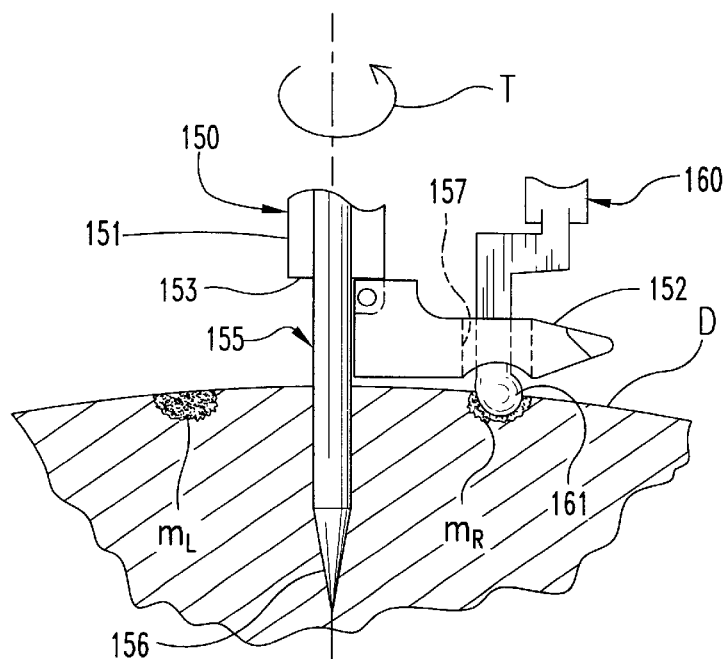
Fig. 15
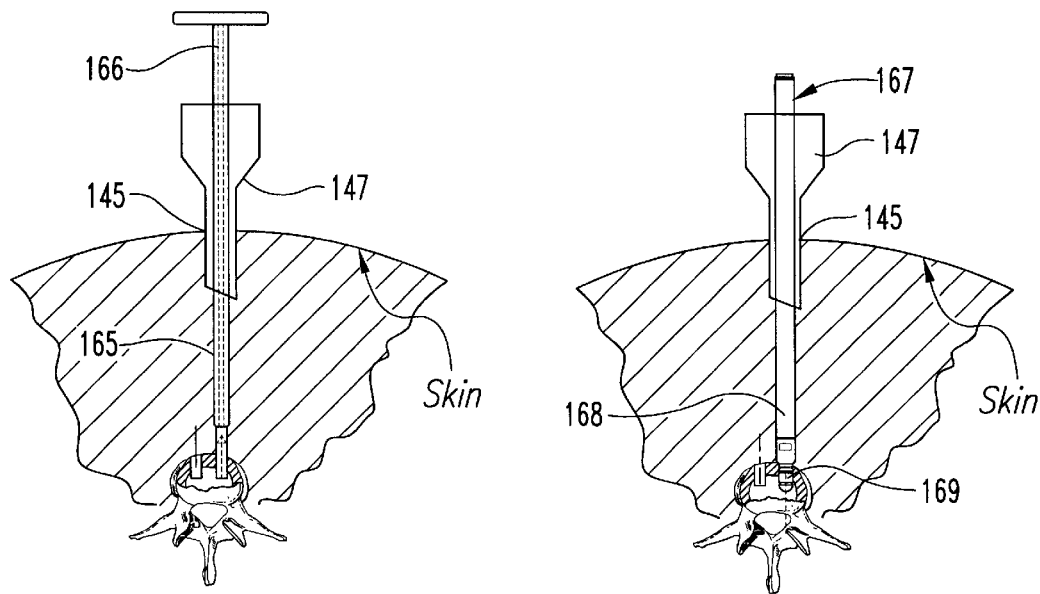
Fig. 17  Fig. 18

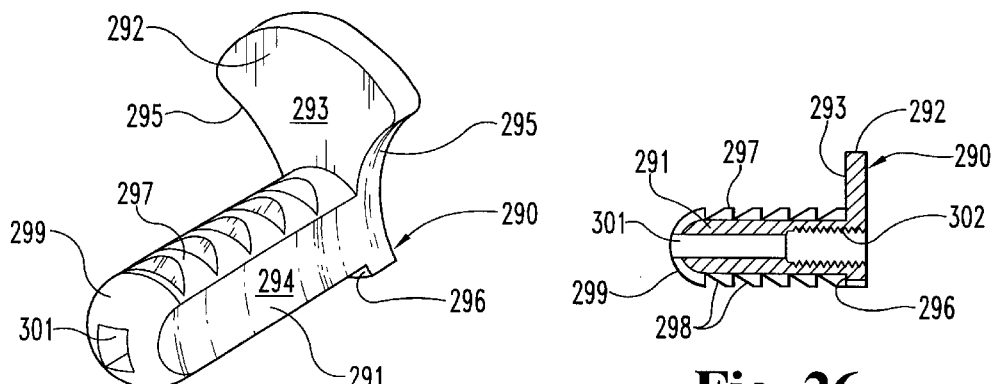
Fig. 25
Fig. 26
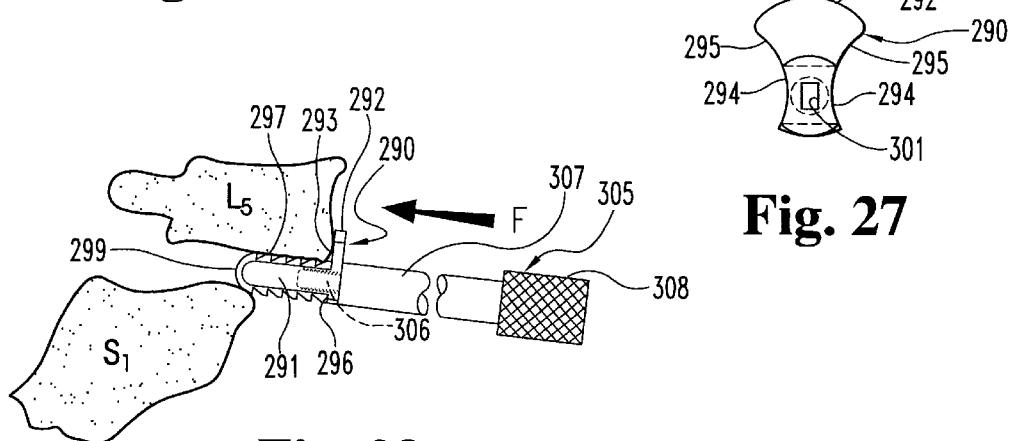
Fig. 27
Fig. 28
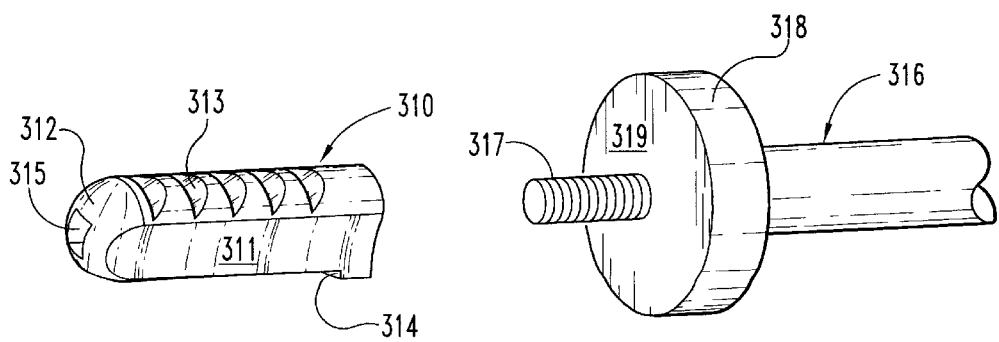
Fig. 29
Fig. 30

METHODS AND INSTRUMENTS FOR INTERBODY FUSION

This application is a divisional application of U.S. patent application Ser. No. 09/781,589, filed on Feb. 5, 2001, now U.S. Pat. No. 6,471,724, which is a divisional application of U.S. patent application Ser. No. 09/014,901, filed on Jan. 28, 1998, now U.S. Pat. No. 6,206,922, which is a continuation-in-part application of U.S. patent application Ser. No. 08/604,874, filed on Feb. 22, 1996, now abandoned, which is a continuation-in-part application of U.S. patent application Ser. No. 08/411,017, filed on Mar. 27, 1995, now U.S. Pat. No. 5,782,919, the contents of each application hereby being incorporated by reference.

This application is a continuation-in-part of application Ser. No. 08/604,874, filed on Feb. 22, 1996, which is a continuation-in-part of application Ser. No. 08/411,017, filed on Mar. 27, 1995, all owned by the assignee of the present application.

BACKGROUND OF THE INVENTION

The present invention relates to methods and instruments for performing an interbody fusion of a disc space between two adjacent vertebrae. Specifically, the invention concerns laparoscopic techniques and instruments to prepare a fusion site and to insert fusion devices and implants.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intradiscal space, otherwise the space may collapse resulting in damage to the nerves extending along the spinal column.

The intradiscal space is often filled with bone or a bone substitute in order to prevent disc space collapse and to promote fusion of the two adjacent vertebrae. In early techniques, bone material was simply disposed between the adjacent vertebrae, typically at the posterior aspect of the vertebrae, and the spine column was stabilized by way of a plate or a rod spanning the affected vertebrae. Once fusion occurred the hardware used to maintain the stability of the segment became superfluous. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably with the need for anterior or posterior plating. There have been an extensive number of attempts to develop an acceptable intradiscal implant that could be used to replace a damaged disc and maintain the stability of the disc interspace between the adjacent vertebrae, at least until complete arthrodesis is achieved. These "interbody fusion devices" have taken many forms. For example, one of the more prevalent designs takes the form of a cylindrical implant. These types of implants are represented by the patents to Bagby, U.S. Pat. No. 4,501,269; Brantigan, U.S. Pat. No. 4,878,915; Ray, U.S. Pat. Nos. 4,961,740 and 5,055,104; and Michelson, U.S. Pat. No. 5,015,247. In these cylindrical implants, the exterior portion of the cylinder can be threaded to facilitate insertion of the interbody fusion device, as represented by the Ray, Brantigan and Michelson patents. In the alternative, some of the fusion implants are designed to be pounded into the intradiscal space and the vertebral end plates. These types of devices are represented by the patents to Brantigan, U.S. Pat. Nos. 4,743,256; 4,834,757 and 5,192,327.

Interbody fusion devices can be generally divided into two basic categories, namely solid implants and implants that are designed to permit bone ingrowth. Solid implants are represented by U.S. Pat. Nos. 4,878,915; 4,743,256; 4,349,921 and 4,714,469. The remaining patents discussed above include some aspect that permits bone to grow across the implant. It has been found that devices that promote natural bone ingrowth achieve a more rapid and stable arthrodesis. The device depicted in the Michelson patent is representative of this type of hollow implant which is typically filled with autologous bone prior to insertion into the intradiscal space. This implant includes a plurality of circular apertures which communicate with the hollow interior of the implant, thereby providing a path for tissue growth between the vertebral end plates and the bone or bone substitute within the implant. In preparing the intradiscal space, the end plates are preferably reduced to bleeding bone to facilitate this tissue ingrowth. During fusion, the metal structure provided by the Michelson implant helps maintain the patency and stability of the motion segment to be fused. In addition, once arthrodesis occurs, the implant itself serves as a sort of anchor for the solid bony mass.

Another interbody fusion device that is designed to permit bone ingrowth is shown in FIG. 1. This device is described and claimed in co-pending parent application Ser. No. 08/411,017, filed on Mar. 27, 1995, which disclosure is incorporated herein by reference. In one embodiment, this invention contemplates a hollow threaded interbody fusion device 10 configured to restore the normal angular relation between adjacent vertebrae. In particular, the device 10 as shown in FIG. 1 includes an elongated body 11, tapered along substantially its entire length, defining a hollow interior 15 and having a largest outer diameter at the anterior end 12 of the device to receive the bone growth material. The body 11 includes an outer surface 16 with opposite tapered cylindrical portions and a pair of opposite flat tapered side surfaces 22 between the cylindrical portions. Thus, at an end view, the fusion device gives the appearance of a cylindrical body in which the sides of the body have been truncated along a chord of the body's diameter.

The cylindrical portions include threads 18 for controlled insertion and engagement into the end plates of the adjacent vertebrae. A started thread 19 is provided at the posterior end 13 of the device 10 to facilitate engagement within a prepared bore. The outer surface of this fusion device is tapered along its length at an angle corresponding, in one embodiment, to the normal lordotic angle of the lower lumbar vertebrae. The outer surface is also provided with a number of vascularization openings 24, 25 defined in the flat side surfaces, and a pair of opposite elongated bone ingrowth slots 27 defined in the cylindrical portions.

Various surgical methods have been devised for the implantation of fusion devices into a subject disc space. A patent to Dr. Gary Michelson, U.S. Pat. No. 5,484,437, discloses one such technique and the associated instruments. As described in more detail in that patent, the surgical technique involved the use of a hollow sleeve having teeth at one end that are driven into the adjacent vertebrae. These teeth and the sleeve maintain the disc space height during the subsequent steps of the procedure. In accordance with one aspect of the invention in the '437 Patent, a drill is passed through the hollow sleeve to remove the disc and bone material to produce a prepared bore for the fusion device. The drill is then removed from the sleeve and the fusion device is positioned within the disc space using an insertion tool.

In another aspect of the procedure and instruments disclosed in the '437 Patent, a long distractor is provided having penetrating portions that urge the vertebral bodies apart to facilitate the introduction of the necessary instruments. The long distractor can act as a guide for drilling and reaming tools concentrically advanced over the outside of the distractor to prepare the site for the fusion device.

While the Michelson technique represents a significant advance over prior surgical procedures for the preparation and insertion of fusion devices, the need for improvement remains. In particular, procedures and instruments that preserve the integrity of the surgical site are desirable. The present invention is directed to this need in the field.

SUMMARY OF THE INVENTION

In accordance with one aspect of the invention, a novel fusion device is provided that integrates a pair of bone screws. The fusion device can be a hollow substantially cylindrical body, such as the device shown in FIG. 1. In this aspect, the device includes a pair of screw bores formed in an end face of the body. The bores are arranged so that bone screws extending through the bores will be driven into the endplates of the adjacent vertebrae. In certain features, the heads of the bone screws are recessed within the body and held in place by a common locking screw. The screws help prevent retrograde expulsion or rotation of the fusion device, or a spacer, from the disc space.

The present invention also contemplates another approach to preventing rotation and/or dislodgment of fusion devices placed bilaterally in the disc space. In one embodiment, a transverse connector plate is engaged by locking screws to the end walls of the bilateral fusion devices. In one feature, the end walls define central recesses and transverse grooves to receive the connector plate. In another embodiment, the connector plate can include screw bores to receive bone screws driven into the vertebrae at a location in between the fusion devices.

In another aspect of the invention, a method is provided for preparing a subject disc space for implantation of a fusion device or implant between adjacent vertebrae. In this technique, a laparoscope is provided that includes an outer sleeve with opposite extensions at one end of the outer sleeve and a laparoscopic port engaged at the outer end of the outer sleeve, the laparoscopic port having a number of seals, with the opposite extensions configured to maintain distraction of the adjacent vertebrae.

The preferred technique comprises the steps of making an incision in the skin of the patient aligned with the subject disc space, retracting tissue beneath the incision to expose the disc annulus; and piercing the disc annulus to create an opening. The outer sleeve of the laparoscope is advanced through the incision, leaving the port outside the skin of the patient while inserting the opposite extensions into the disc space with the outer sleeve contacting the disc annulus. The laparoscope, and particularly, the outer sleeve, creates a protected working channel between the disc space and the laparoscopic port outside the patient.

In a further step of the preferred inventive technique, a reamer is operated through the number of seals and the outer sleeve of the laparoscope to create a prepared bore in the disc material and the adjacent vertebrae for implantation of a device into the bore.

In a most preferred embodiment of the surgical technique, the technique comprises the steps of percutaneously exposing the annulus of the disc in the subject disc space through an incision in the skin of the patient and piercing the disc annulus to create an opening. A distractor can then be inserted through the incision and through the opening into the disc space to distract the vertebrae adjacent the subject disc space. The laparoscope outer sleeve is then introduced through the incision and over the distractor, leaving the port outside the skin of the patient while inserting the opposite extensions through the opening into the disc space to create the protected working channel between the port and the distractor tip.

In subsequent steps, the distractor is removed and a reamer is advanced through the number of seals of the laparoscope and through the outer sleeve into the disc space to ream the disc space and adjacent vertebrae to create a prepared bore for the fusion implant. After the reamer is removed from the laparoscope, the fusion implant can be advanced through the number of seals and through the outer sleeve into the prepared bore. With the fusion implant in position, the laparoscope can be withdrawn from the patient.

In one aspect of the invention, a switching sleeve is placed within the outer sleeve of the laparoscope with an end of the switching sleeve projecting beyond the opposite fingers of the outer sleeve, the end of the switching sleeve being tapered to minimize trauma to tissue adjacent the subject disc space as the outer sleeve adjacent into the patient with the switching sleeve projecting beyond the opposite extensions of the outer sleeve.

In a further embodiment, the laparoscopic method is used for bilateral placement of two fusion devices into a subject disc space. In addition to the steps previously described, this embodiment of the surgical technique includes unseating the outer sleeve of the laparoscope from the first opening in the disc annulus by withdrawing the laparoscope until the opposite extensions of the outer sleeve are outside the disc annulus. With the switching sleeve in position within the outer sleeve, the laparoscope is moved to the second opening in the disc space without removing the laparoscope from the patient. The steps for preparing the bore to receive a fusion implant can be repeated. In one specific embodiment, these steps are conducted at the second opening with the distractor remaining within the first opening. After a fusion implant is advanced through the number of seals and through the outer sleeve into the second prepared bores the laparoscope can then be returned to the first opening for insertion of another fusion implant. During this step, the fusion implant contained within the second prepared bore maintains distraction of the disc space.

As an adjunct to this inventive technique, a distraction device is provided in one aspect of the invention. The distraction device can include an elongated stem sized for insertion along the A-P midline of the intervertebral disc space. Preferably, opposite surfaces of the device include a number of ridges that operate as bone engaging surfaces to resist expulsion of the device. In one important feature, the stem of the distraction device includes a bore to receive a spike projecting from a tubular body, such as the outer sleeve discussed above. With this feature, the distraction device acts not only as a midline distractor, but also as a centering guide to locate the tubular body through which subsequent surgical procedures can be performed.

In a further feature, the distraction device can include a flange projecting from the stem. The flange has a bone contacting that transmits to the vertebra a force applied to the distraction device (preferably by a manual tool). This flange can be used to reduce a high grade spondylolisthesis condition as the distraction device is driven into the disc space.

One object of the present invention is to provide surgical technique and instruments that permit the preparation of a disc space for insertion of a fusion implant under a sealed condition. A further object of the invention is to implement laparoscopic techniques to implant fusion devices.

With respect to fusion devices, one object is to enhance the stability of the device in situ while reducing the risk of expulsion of the device. Yet another object is to provide means for readily reducing a spondylolisthesis condition from a laparoscopic approach.

One benefit of the present invention is that all of the steps necessary to prepare a disc space and to implant a fusion device can be conducted in a protected environment. In addition, the inventive techniques and instruments allow minimal intrusion into the patient, which minimized the risks normally associated with spinal surgery.

Other objects and benefits can be discerned from the following written description and accompanying figures.

DESCRIPTION OF THE FIGURES

FIG. 2 is a top elevational view of an implant driver for use in engaging and driving a fusion device such as the device shown in FIG. 1.

FIG. 3 is an enlarged perspective view of the end of the implant driver shown in FIG. 2 engaged to a fusion device such as shown in FIG. 1.

FIG. 4 is an enlarged side cross-sectional view of the implant driver and fusion device shown in FIG. 3.

FIG. 8 is an end perspective view of a threaded fusion device according to a further embodiment of the invention.

FIG. 9 is a side perspective view of a driving tool attachment according to a further aspect of the present invention in which the driving tool attachment is configured to engage the fusion device depicted in FIG. 8.

FIG. 10 is a side partial cross-sectional view of a fusion device according to the embodiment of FIG. 8 disposed between adjacent vertebrae and engaged in position by a pair of bone screws in accordance with one aspect of the present invention.

FIG. 13 is a frontal view of a patient with locations identified for surgical incisions according to a preferred embodiment of the present inventive laparoscopic surgical technique.

FIG. 14 is an A-P representation of a spinal segment at the laparoscopic surgical site depicting one step of the inventive surgical technique in which bilateral locations are marked on the disc annulus for insertion of a pair of fusion devices, such as the device shown in FIG. 1.

FIG. 15 is an enlarged A-P view of the disc at the spinal segment showing the use of the template represented in FIG. 14 of the invention.

FIG. 16 is an A-P representation of the laparoscopic surgical site depicting a further step of the inventive surgical technique of creating a pilot hole at each of the bilateral locations marked in the step shown in FIG. 14.

FIG. 17 is an A-P representation of the laparoscopic surgical site depicting a further step of the inventive surgical technique of using a trephine to create a bore at each of the bilateral locations marked in the step shown in FIG. 14.

FIG. 18 is an A-P representation of the laparoscopic surgical site depicting a further step of the inventive surgical technique for inserting a distractor into the prepared site at each of the bilateral locations marked in the step shown in FIG. 11.

FIG. 25 is a top perspective view of a distraction plug in accordance with one embodiment of the present invention.

FIG. 26 is a side cross-sectional view of the distraction plug shown in FIG. 25.

FIG. 27 is an end elevational view of the distraction plug shown in FIGS. 25 and 26.

FIG. 28 is a side view of the distraction plug shown in FIG. 25 as it is inserted between adjacent vertebrae using a plug driver in accordance with one aspect of the present invention.

FIG. 29 is a side perspective view of a distraction plug in accordance with a further embodiment of the present invention.

FIG. 30 is a side perspective view of a plug driver in accordance with a further embodiment of the invention configured for engaging a distractor plug as shown in FIG. 29.

DESCRIPTION OF THE PREFERRED EMBODIMENTS

Figure 1:
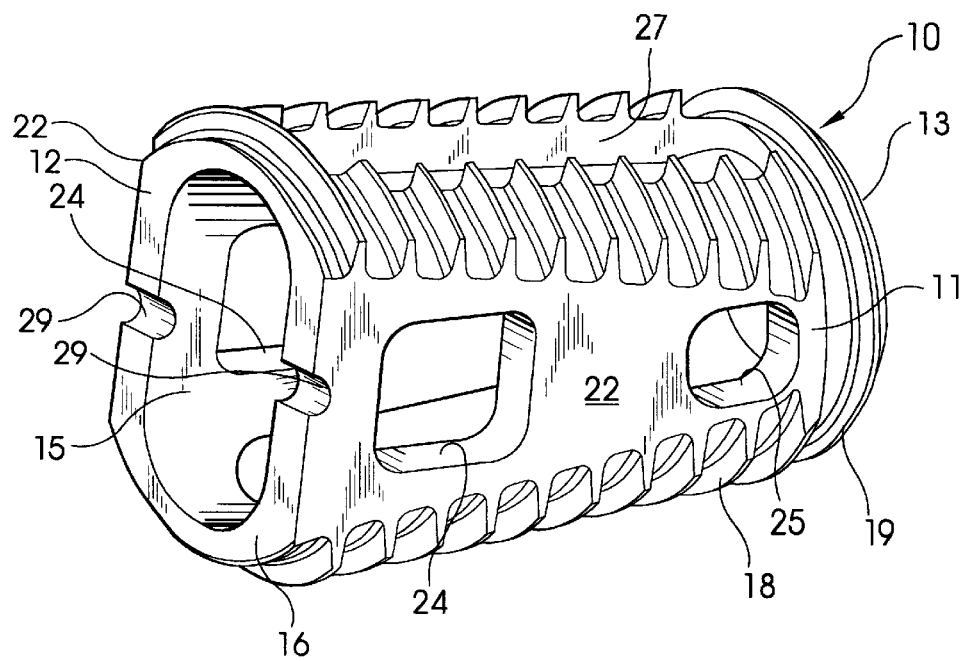
FIG. 1 is a side perspective view of a threaded fusion device having a tapered configuration to restore the normal angle of a spinal motion segment.

For the purposes of promoting an understanding of the principles of the invention, reference will now be made to the embodiments illustrated in the drawings and specific language will be used to describe the sane. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As described above, one interbody fusion device, as shown in FIG. 1, can be implanted within the intradiscal space. This interbody fusion device 10 can be implanted using the implant driver 50 shown in FIG. 2. The implant driver 50 is comprised of a shaft 51 and sleeve 52 concentrically disposed about the shaft. Tongs 54 are formed at one end of the shaft for gripping the interbody fusion device 10 for implantation. Preferably the tongs include a tapered outer surface 55 and an opposite flat inner surface 56 adapted to engage the truncated side walls 22 of the interbody fusion device as shown in FIGS. 3, 4. Most preferably the tapered outer surface 55 conforms to the root diameter of the interrupted threads 18 of the device 10 so that the tongs 54 essentially complete the full cylindrical shape of the body wall 16. The adaptation of the tongs' tapered outer surface 55 facilitates screw insertion of the interbody fission device 10 since the outer surface 55 will ride within the tapped bore in the vertebral end plates.

Each of the tongs 54 can be provided with interlocking fingers 58 and a driving projection 59 extending from the inner surface 56, most clearly shown in FIG. 4. Referring again to FIG. 2, the shaft 51 defines a hinge slot 62 supporting each of the pair of tongs 54. The hinge slot 62 is configured so that the tongs will have a naturally biased position spread sufficiently apart to accept the fusion device 10 therebetween. The shaft 51 defines a conical taper 63 between the hinged slot 62 and each of the tongs 54. This conical taper mates with a conical chamfer 67 defined on the inner wall of the sleeve 52. Thus, as the sleeve 52 is advanced toward the tongs 54, the conical chamfer 67 rides against the conical taper 63 to close or compress the hinge slot 62. In this manner, the tongs 54 are pushed toward each other and pressed into gripping engagement with the interbody fusion device situated between the tongs.

The shaft 51 and sleeve 52 are provided with a threaded interface 65 which permits the sleeve 52 to be threaded up and down the length of the shaft. Specifically, the threaded interface 65 includes external threads on the shaft 51 and internal threads on the sleeve 52 having the same pitch so that the sleeve can be readily moved up and down the implant driver 50. The shaft 51 is also provided with a pair of stops 69 which restrict the backward movement of the sleeve 52 to only the extent necessary to allow the tongs 54 to separate a sufficient distance to accept the interbody fusion device 10.

The use of the implant driver 50 is shown with reference to FIGS. 3, 4. As can be seen in FIG. 3, the outer surface 55 of the tongs 54 reside generally flush with the root diameter of the interrupted threads 18. As seen in FIG. 4, the interlocking fingers 58 can be arranged to fit within the vascularization opening 24 on each of the truncated side walls 22. In a similar fashion, the driving projections 59 engage the driving tool slots 29 at the anterior end 12 of the conical body 11. The combination of the interlocking fingers 58 and driving projections 59 firmly engage the interbody fusion device 10 so that the device can be screw threaded into a tapped or untapped opening in the vertebral bone. The tongs 54 in this embodiment are configured to engage the fusion device 10 and to impart a threading or rotational force to the device. It is understood that the tongs can adopt other configurations depending upon the structure of the fusion device to be implanted.

Figure 5:
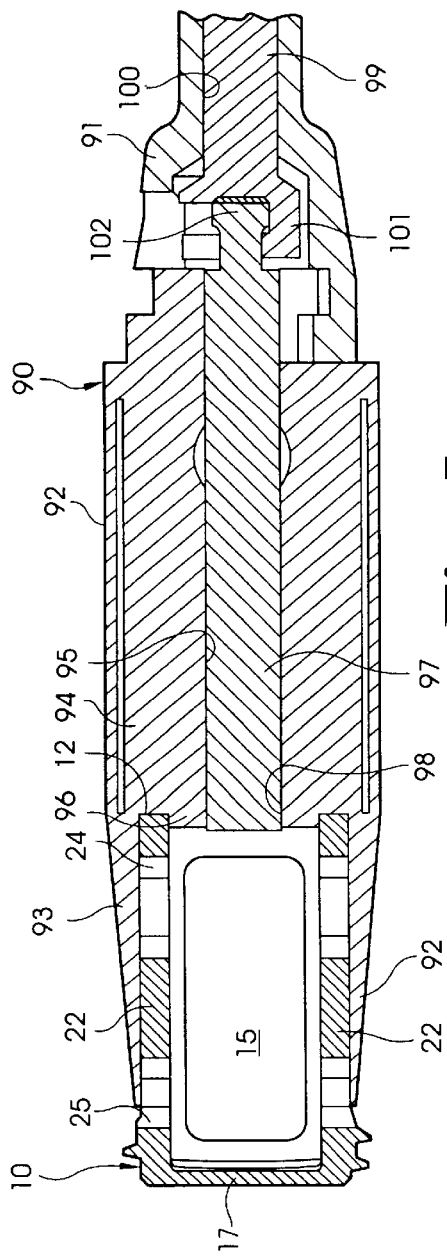
FIG. 5 is an enlarged side cross-sectional view of an alternative embodiment of an implant driver for engaging and driving a fusion device such as the device shown in FIG. 1.

An alternative embodiment of the implant driver is shown in FIG. 5. The driver 90 includes a shaft 91, having a length sufficient to reach into the intradiscal space from outside the patient. Connected to the end of shaft 91 is a head which defines a pair of opposite tongs 93, each of which are configured for flush contact with the flat truncated side walls 22 of the fusion device 10. Like the tongs 54 of the previously described implant driver 50, the outer surface of the tongs is cylindrical to correspond to the cylindrical threaded portion of the device.

Unlike the implant driver 50, the driver 90 of the embodiment in FIG. 5 uses an expanding collet assembly to firmly grip the fusion device 10 for insertion into the body. Specifically, the head 92 defines a collet 94 having a central collet bore 95 formed therethrough. The collet 94 terminates in an annular flange 96 that at least initially has a diameter slightly smaller than the inner diameter of the fusion device 10 at its end 12. An expander shaft 97 slidably extends through the collet bore and includes a flared tip 98 situated adjacent and extending just beyond the annular flange 96. The flared tip 98 of the expander shaft 97 starts at a diameter sized to slide within the collet bore 95 and gradually flares to a diameter larger than the bore.

The implant driver 90 further includes a puller shaft 99 slidably disposed within a bore 100 defined in the shaft 91. The puller shaft 99 has a locking chamber 101 at its end which engages a locking hub 102 formed at the end of the expander shaft 97. The puller shaft 99 projects beyond the end of the shaft 91 for access by the surgeon. When the puller shaft 99 is pulled, it pulls the expander shaft 97 away from the annular flange 96 of the collet 94 so that the flared tip 98 becomes progressively engaged within the collet bore 95. As the tip 98 advances further into the bore 95, the annular flange 96 expands from its initial diameter to a larger second diameter sufficient for firm gripping contact with the interior of the fusion device 10. With the fusion device so engaged, the implant driver can be used to insert the device 10 into the surgical site, after which the expander shaft can be advanced beyond the collet bore to release the flat tip and, consequently, the fusion device.

Figure 6:
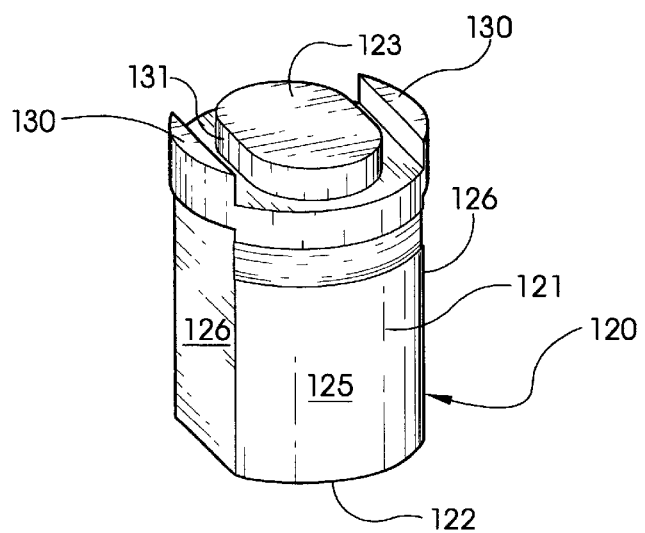
FIG. 6 is a driving tool attachment according to one aspect of the present invention.

In certain circumstances, it may be necessary to drive the fusion device 10 deeper into the disc space. When either of the implant drivers 50 or 90 is engaged to the fusion device, the device can be readily advanced farther into the disc space. However, once the implant driver is removed and it is then discovered that the fusion device needs to be repositioned, the flexible nature of the tongs 54 and 93 of the two implant drivers makes reacquisition of the now implanted fusion device difficult. To alleviate this difficulty, a driving tool attachment 120 is provided, as shown in FIG. 6. The driving tool attachment 120 includes a body 121 having a first end 122 and an opposite second end 123. Like the fusion implant, the body 121 of the driving tool attachment 120 includes a cylindrical portion 125 and opposite flat side portions 126. The opposite side portions 126 are configured to be engaged by the tongs of the above driving tools 50 or 90.

The driving tool attachment 120 includes a pair of opposing flanges 130 at end 123. The flanges 130 are configured to engage the opposite flat surface 122 on the fusion implant 10, in a manner similar to that accomplished by the tongs of the implant driver 50 and 90. The end 123 also includes a boss 131 which is configured to be inserted into the opening at the end of the implant 10 (see FIG. 7).

Figure 7:
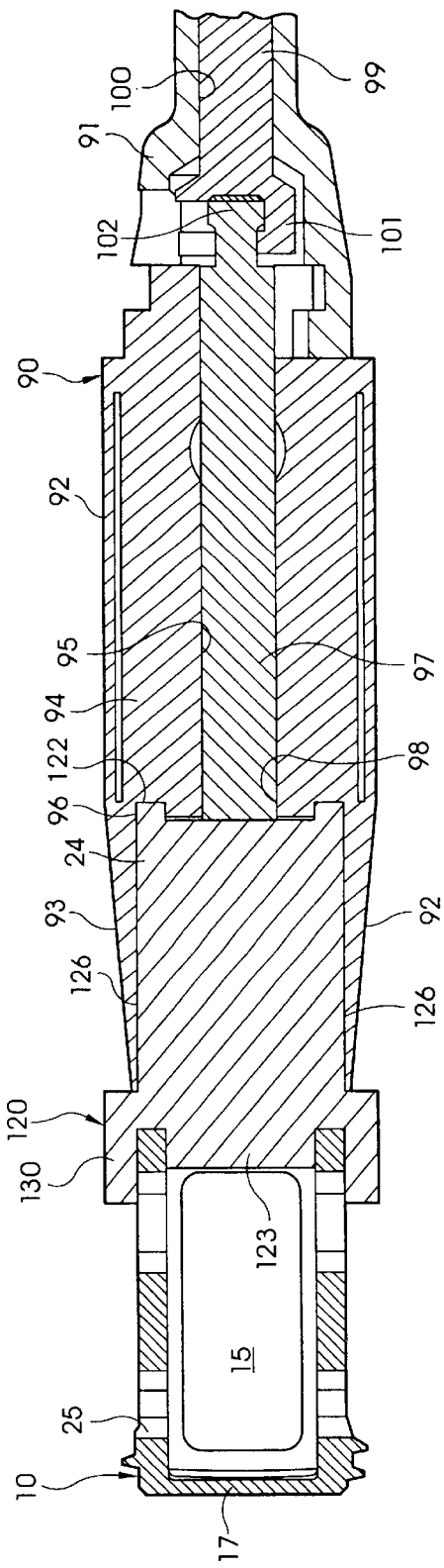
FIG. 7 is an enlarged side cross-sectional view similar to the view in FIG. 5 with the driving tool attachment of FIG. 6 engaged between the implant driver and the fusion device.

In use, the driving tool attachment 120 can be engaged with one of the driving tools 50 or 90, with the tongs firmly grasping the flat surfaces 126, as shown in FIG. 7. The driving tool attachment can then be advanced into the disc space with the flanges 130 oriented across the space so that they can readily interface with the flat surfaces 22 of the fusion device 10. When the driving tool attachment 120 is properly aligned, the boss 131 projects into the hollow opening 15 at the anterior end 12 of the fusion device and the flanges 130 engage the opposite flat surfaces 22 of the device. The driving tool can then be rotated as if the fusion implant were directly engaged to the main driving tool. The attachment readily transmits the rotational driving force to the implant 10 to thread it deeper into the disc space or to retract it back within the disc space. One particular advantage provided by the driving tool attachment 120 is that the relatively flexible tongs of the two driving tools 50 and 90 can be already engaged to the attachment 120 before insertion into the surgical site. This eliminates a great deal of fiddle factor and avoids the risk that the tongs would be unable to firmly grasp the implant 10 when it is already in position within the disc space.

In a further embodiment of the present invention, an interbody fusion device is provided that permits supplemental fastening to the adjacent vertebrae. In particular, an interbody fusion device 250, as depicted in FIG. 8, includes a hollow body 251 having a first end 252 and a second end 253. The hollow body 251 defines a hollow interior 255 and includes an end wall 256 at the first end 252. Like the fusion device 10 shown in FIG. 1, the interbody fusion device 250 includes external threads 258 spanning a substantial portion of the length of the hollow body 251, and a continuous thread 259 adjacent the second end 253 of the body. Also like the fusion device 10, the interbody fusion device 250 includes opposite flat sidewalls 262 that interrupt the external threads 258, as well as opposing slots 263 offset from the flat sidewalls 262 which also interrupts a portion of the external threads 258. Thus far, the interbody fusion device 250 is substantially similar to the device 10 shown in FIG. 1. For example, the device can be tapered so that it has a larger diameter at the first end 252 than at the second end 253. In addition, side windows 264 (see FIG. 10) can be provided in the flat sidewalls 262. The side walls 262 essentially divide the body 251 into upper and lower threaded portions that are configured to be threadedly driven into adjacent vertebrae.

In accordance with this embodiment, the interbody fusion device 250 includes a pair of driver openings 265 defined in the end wall 256 at the first end 252. Intermediate between the driver openings 265 are a pair of offset screw bores 267. In this preferred embodiment, the screw bores 267 are formed so that their respective longitudinal axes intersect and project out from the top and bottom portions 260, 261. Preferably the axes are arranged to intersect the slots 263 in the top and bottom of the fusion device. In this configuration, the longitudinal axes of the two screw bores intersect outside the hollow body 251 and the end wall 256, as seen in FIG. 10. A threaded bore 270 is formed between the two screw bores 267. The screw bores 267 also define a recessed portion 268, while the threaded bore defines a recessed portion 271 that intersects each of the recessed portions 268 of the screw bores 267 at an overlap 272.

In using the interbody fusion device 250, a driving tool attachment 275 is provided that permits insertion of the device within a properly prepared intervertebral space. As depicted in FIG. 9, the driving tool attachment 275 is similar to the implant driver shown in FIG. 6. In this instance, the driving tool attachment 275 includes a body 276 having opposite flat sidewalls 277, so that the body is adapted to be engaged by the implant driver 90 in the manner depicted in FIG. 7. In accordance with the present embodiment, the driving tool attachment 275 includes a pair of spaced-apart driving bosses 278 projecting from a mating face 279. The bosses 278 are sized and shaped to fit within the driver openings 265 when the mating face 279 is in direct contact with the end wall 256 of the fusion device 250. The driving tool attachment 275 can be engaged to a fusion device, such as device 250, to permit threading of the device into the intervertebral disc space, such as the space between lumbar vertebrae L4 and L5, as shown in FIG. 10.

With the fusion device 250 appropriate positioned within the intervertebral disc space, a pair of bone screws 280 can be extended through respective screw bores 267 in the hollow body 251. The screws are passed through the bores 267 until the bone engaging threads of the screws 280 contact the vertebral bone. As the bone screws 280 are threaded into the vertebral bone, the head 281 of each of the bone screws 280 seats within the respective recessed portions 268 of each of the screw bores 267. In this orientation, the heads 281 of the bone screws 280 are flush with or below the surface of the end wall 256 of the fusion device 250. At this point, a locking screw 282 can be threaded into the threaded bore 270. As the locking screw is tightened into the bore 270, the head 283 of the locking screw contacts the heads 281 of both bone screws 280. Further tightening of the locking screw 282 causes the head 283 to seat within the recessed portion 271 to trap the heads 281 of the bone screws 280 within their respective screw bores 267. Thus, the set screw 282 prevents backout of the bone screws 280 when they are engaged within the adjacent vertebrae.

The diverging bone screws 280 provide greater stability to the fusion device 250 than can be achieved with prior threaded devices. The bone screws enhance the resistance to retrograde expulsion of the device and prevents counter-rotation or unthreading. The bone screws 280 can be of a wide range of sized provided that the screws are long enough to achieve an effective purchase in the adjacent vertebrae.

Figure 11A:
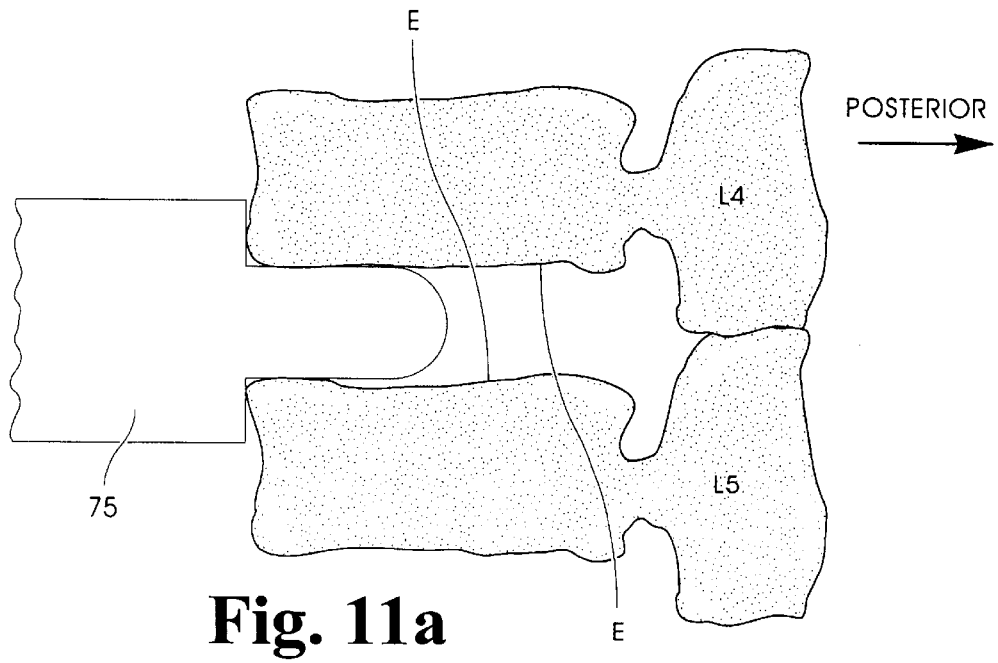
FIGS. 11(a)–(d) are lateral representations of the spine showing four steps of a surgical method for implanting a fusion device such as the device in FIG. 1 according to an anterior approach in one aspect of the present invention.
Figure 11B:
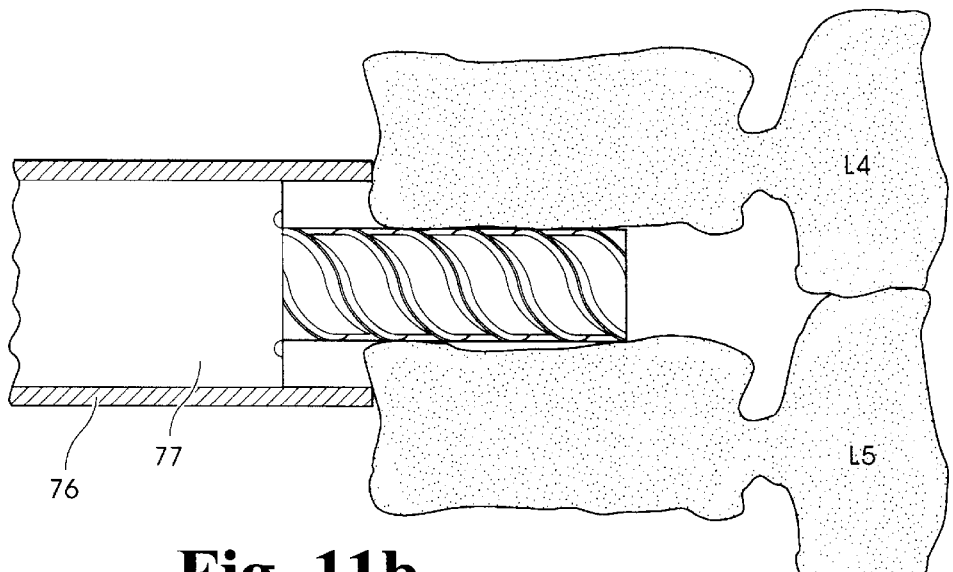

In accordance with additional aspects of the present invention, two methods for implanting an interbody fusion device, such as the devices 10 or 250, are contemplated. First, with reference to FIGS. 11(a)–11(d), an anterior approach is shown. As a preliminary step, it is necessary to locate appropriate starting points for implanting the fusion device, preferably bilaterally. In the first step of the anterior approach, a distractor 75 is disposed between the vertebral end plates E to dilate the L4–L5 or L5–S1 disc space. (It is understood, of course, that this procedure can be applied at other vertebral levels). In the second step, shown in FIG. 11(b), an outer sleeve 76 is disposed about the disc space. The outer sleeve 76 can be configured to positively engage the anterior aspect of the vertebral bodies to firmly, but temporarily, anchor the outer sleeve 76 in position. In essence, this outer sleeve 76 operates as a working channel for this approach. In the step of FIG. 11(b), a drill 77 of know design is extended through the outer sleeve and used to drill out circular openings in the adjacent vertebral bodies. The openings can be tapped to facilitate screw insertion of the fusion device 10, although this step is not necessary.

Figure 11C:
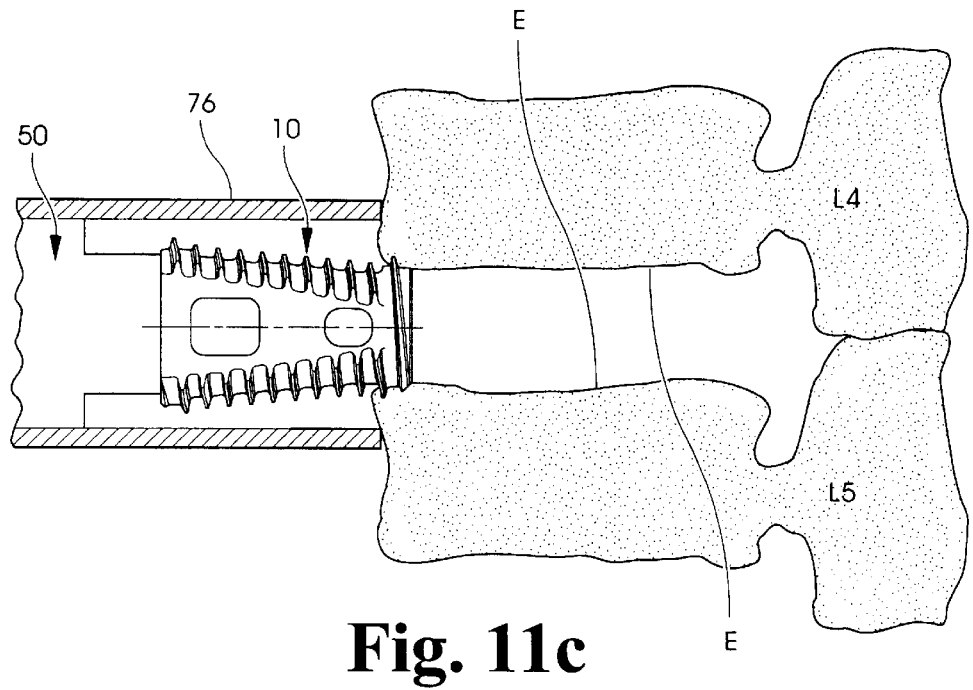
Figure 11D:
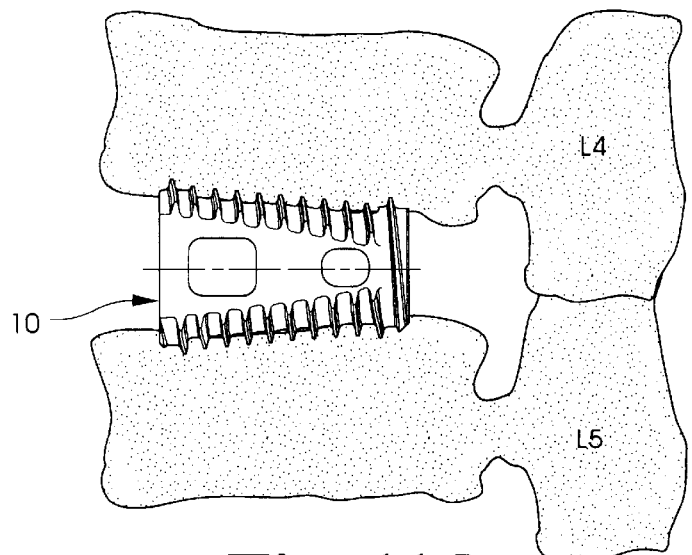

In the next step shown in FIG. 11(c), the fusion device 10 is engaged by the implant driver 50 and extended through the outer sleeve 76 until the starter thread 19 contacts the bone opening. The implant driver 50 can then be used to screw thread the fusion device into the tapped or untapped opening formed in the vertebral end plate E. It is understood that in this step, other suitable driving tools could be used, such as a screw driver configured to engage the driving tool slots 29 at the anterior end 12 of the device 10. The degree of insertion of the fusion device 10 determines the amount of lordosis added or restored to the vertebral level. In the final step, the implant driver is removed leaving the fusion device 10 in position. It can be seen that once implanted, the closed posterior end 13 is directed toward the posterior aspect of the vertebrae. The hollow interior 15 is open at its anterior end 12, but can be closed by a plastic or metal material, if necessary.

Figure 12A:
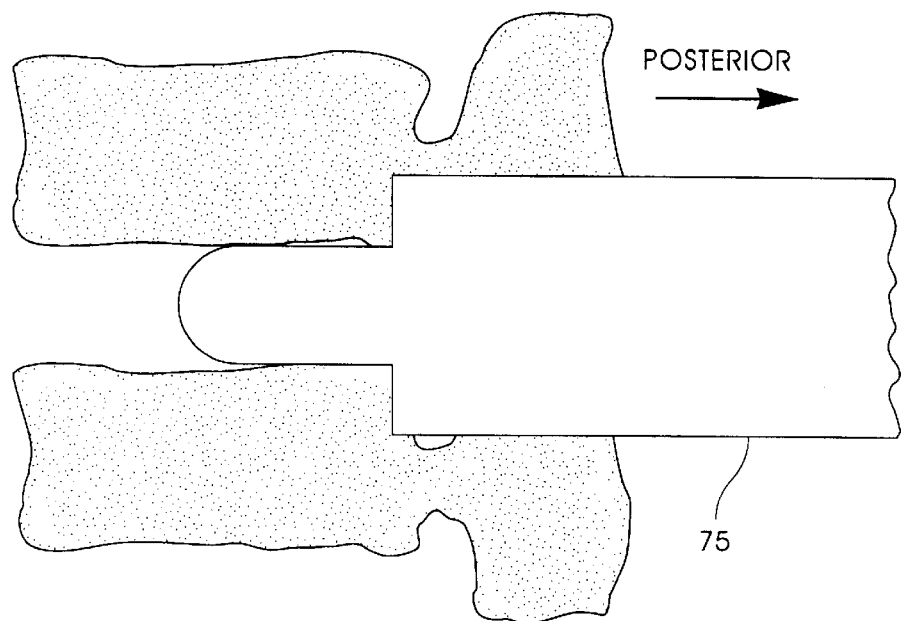
FIGS. 12(a)–(d) are lateral representations of the spine showing four steps of a surgical method for implanting a fusion device such as the device in FIG. 1 according to a posterior approach in a further aspect of the present invention.
Figure 12B:
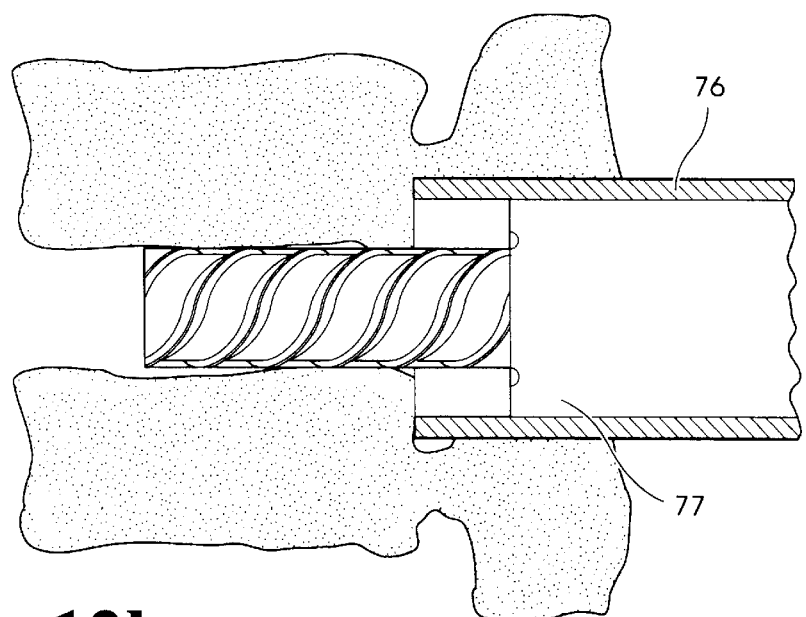
Figure 12C:
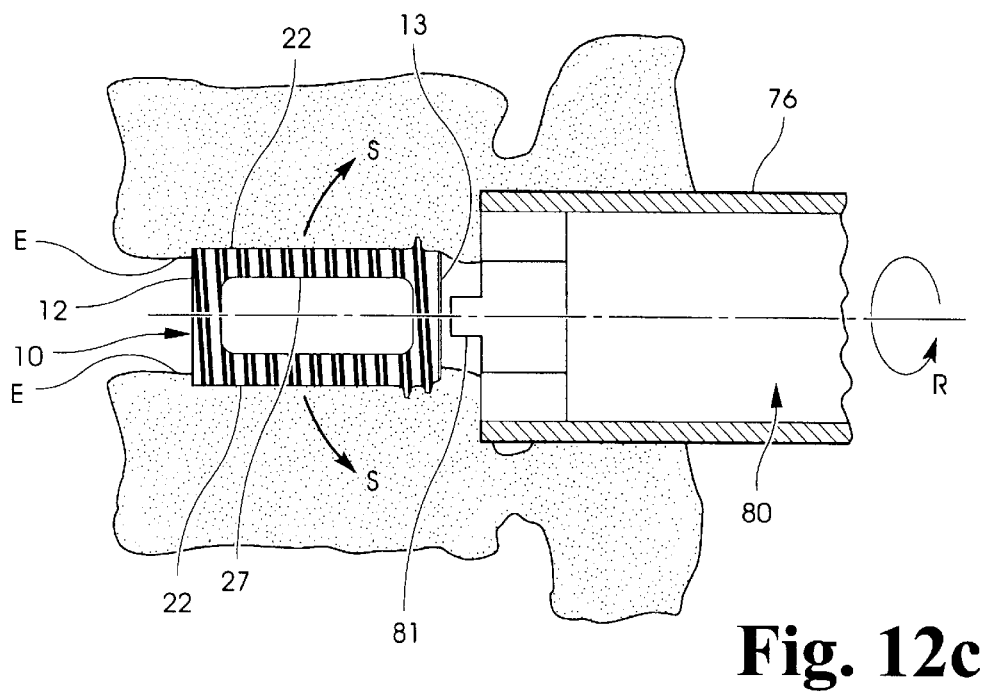
Figure 12D:
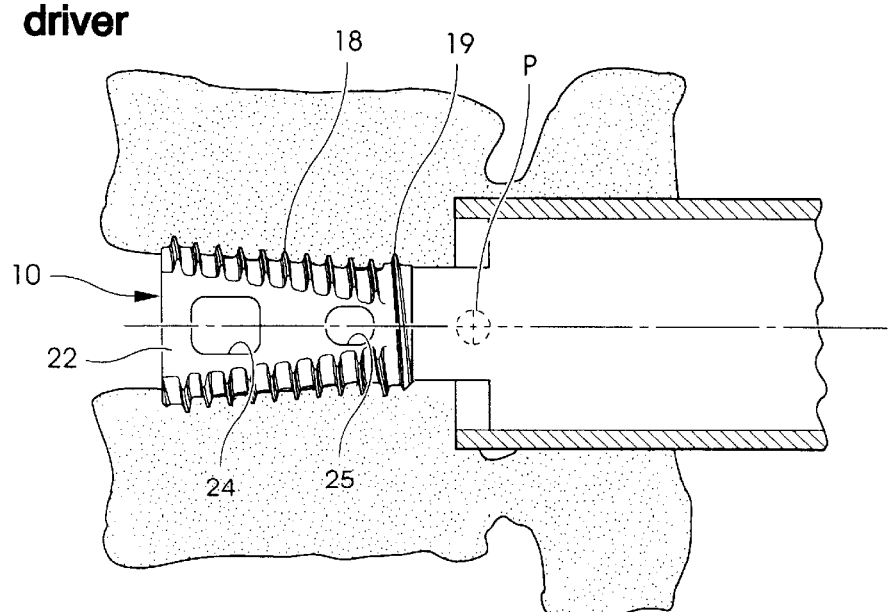

In a second inventive method, as depicted in FIGS. 12(a)–12(d), a posterior approach is implemented. The first two steps of the posterior approach are similar to that of the prior anterior approach, except that the distractor 75, outer sleeve 76 and drill 77 are introduced posteriorly at the instrumented motion segment. This approach may require decortication and removal of vertebral bone to accept the outer sleeve 76. In the third step of this method, the fusion device 10 is inserted through the outer sleeve 76 into the dilated disc space. It is understood that the disc space is preferably dilated only to the extent necessary to receive the implant with the truncated side walls 22 directly facing the vertebral end plates E. Thus, as shown in FIG. 12(c), the bone ingrowth slot 27 is facing laterally, rather than coronally, as expected for its final implanted position. A suitable driving tool 80 can be provided to project the fusion device 10 through the outer sleeve 76 and into the intradiscal space. In one embodiment, the driving tool 80 includes a projection 81 which is configured to engage a slot opening formed in the end wall at the posterior end 13 of the fusion device 10. An internal thread (not shown) can be used to fix the device 10 to the driver 80.

Once the fusion device 10 has been advanced into the intradiscal space to the appropriate depth relative to the pivot axis P of the vertebrae, the driving tool 80 is used to rotate the implant in the direction of the rotational arrow R in FIG. 12(c). As the driving tool 80 is rotated, the device itself rotates so that the interrupted threads 18 start cutting into the vertebral bone at the end plates E. In this manner, the implant operates as a cam to separate the adjacent vertebrae in the direction of the spreading direction arrows S in FIG. 12(c). This camming approach provides a somewhat easier insertion procedure than for the anterior approach of FIGS. 11(a)–(d) in that a single rotation is required to lock the implant into the vertebral bone. In contrast, the formerly discussed screw insertion technique of the anterior approach requires continuous threading of the device into position.

With either the anterior (FIGS. 11(a)–(d)) or the posterior approach (FIGS. 12(a)–(d)), the position of the fusion device 10 with respect to the adjacent vertebrae can be verified by radiograph or other suitable techniques for establishing the angular relationship between the vertebrae. Alternatively, the preferred depth of insertion of the implant can be determined in advance and measured from outside the patient as the implant is positioned between the vertebrae. The depth of insertion of the fusion device can be ascertained using depth markings (not shown) on the implant drivers 50, 90 or 80.

In another embodiment of the inventive surgical technique, laparoscopic technology is used to provide a sealed and protected channel for instruments and implants directed to the subject disc space. In accordance with one aspect of this inventive method, an anterior approach to the L5–S1 motion segment is illustrated. It is of course understood that these same techniques and instruments to be described below could be used at different vertebral levels or in a posterior approach under appropriate conditions.

As depicted in FIG. 13, the present inventive technique includes making a small incision 140 and preferably inserting an insufflator needle into the abdominal cavity. Fluid is introduced into the abdominal cavity through the insufflator needle to a pressure of preferably approximately 15 mm of mercury to assist in visualization of the surgical site. An initial port 141 for the laparoscope is placed five to ten centimeters cephalad of the umbilicus in the midline ten millimeters in length. The abdomen is visually explored and the patient is placed in steep Trandelenburg. The abdominal wall is visualized endoscopically as two working ports 142, 143 are placed just lateral to the epigastric vessels, opposite the level or levels to be fused. It is believed to be advantageous to stagger the ports slightly from direct opposition to each other.

The preferred method continues with insertion of retractors through the ports 142, 143. The retractors can be used to sweep the small bowel superiorly out of the pelvis. The sigmoid colon is also pulled out of the pelvis and held laterally with the left fan retractor. For fusion at the L5–S1 junction, the sacral promontory and drop-off can be easily seen at this point. The posterior peritoneum overlying the L5–S1 disc space is then incised longitudinally with endoshears for the desired exposure. Using opposing fan retractors as blunt dissectors, the soft tissue underlying the parietal peritoneum can be swept laterally to bilaterally expose the anterior L5–S2 disc annulus. The sacral artery and vein coursing the disc are individually ligated with hemoclips and transected. A dissector can be used to remove residual soft tissue over the disc. Exposure is maintained with the left fan retractor in place holding the colon out of the way. It has been found that usually the right side does not require retraction, so a suction irrigation catheter can be used through this port.

In one specific procedure for the L4–L5 disc, the posterior peritoneum is incised more proximally about 3 centimeters. Again, the left fan is used to retract the colon laterally and with careful blunt dissection the aorta is exposed anteriorly at the bifurcation. The L4–L5 disc is usually right below this point. Left lateral dissection is carried out over the left common iliac vein and artery, gently retracting these vessels to the right. In order to retract these vessels enough to the right for adequate disc exposure the ascending segmental vein branch must be identified and transected. Once this vessel is cut, the artery and vein can then be bluntly retracted to the right with a fan or loop retractor to expose a significant amount of the L4–L5 disc for fusion.

Once the subject disc is exposed, it can be important to align the abdominal entry operating trocar port site 145 with the disc to be fused so that the operating trocar is parallel with the endplates of the disc in the sagittal plane. The entry point is estimated and a small Steinmann pin can be placed either in the interspace or along the patient and checked with lateral C-arm and adjusted accordingly. A 1.5 to 2.5 centimeter incision can be made for placement of the operating trocar. A blunt introducer is placed in the abdomen and an 18 mm working trocar 147 (FIG. 14) can be placed over it under endoscopic visualization.

In accordance with a further aspect of the present embodiment of the surgical technique, the annular of the subject disc D is marked for bilateral placement of a pair of fusion devices. For example, as shown in FIG. 14, a working trocar 147 is situated within the working port 145 (see FIG. 13). The bilateral marks can be made with a template 150, as shown in general in FIG. 14 and in more detail in FIG. 15. Greater detail concerning this template and its method of use can be found in U.S. Pat. No. 5,645,549, issued on Jul. 8, 1997. The description of this template in this co-pending application is incorporated herein by reference.

For convenience, a brief description of the template will be made with specific reference to FIG. 15. In particular, the template 150 includes tubular body 151 and an elongated guide foot 152 that is pivotable connected to the end 153 of the tubular body. A guide wire or stylet 155 extends through the tubular body to pivot the foot 152 to the side. The sharp tip 156 of the stylet can then be used to pierce the disc annulus D. Using a mallet, the template can be secured to the center of the disc space by driving the stylet 156 into the disc tangential to the curvature of the annulus and parallel to the endplates. The template can then be slide down the guide wire or stylet until the foot 152 contacts the disc annulus.

The foot includes an opening 157 through which an electrocautery device 160 can extend. The tip 161 of the electrocautery device is guided through the opening 157 in the foot 152 to contact the disc annulus D. When the tip 161 is energized, it leaves a mark MR that is lateral to the center of the subject disc. The template 150 can then be rotated in the direction of the arrow T so that the foot is situated laterally opposite the first mark MR. At that point, the electrocautery device can be used to make a second mark ML providing the bilateral positions for the two fusion devices.

Once the bilateral marks MR, ML have been made on the disc annulus, the surgeon has a visual indication as to the proper location for placement of the fusion device. Under direct visualization of the insufflated abdominal region by way of a laparoscope through port 141 (FIG. 13), the surgeon can then direct a T-handle probe 160 through the working port 147 to the either of the cauterization marks MR and ML (FIG. 16). The T-handle probe 160 includes a sharp tip 161 that is used to break through the disc annulus. The T-handle allows the surgeon to rotate the probe 160 as necessary to facilitate penetration into the annulus. Once an initial opening has been made in the disc annulus by way of the T-handle probe 160, a T-handle trephine 165 can be used to create pilot holes for subsequent instrumentation. The T-handle trephine 165 can include a series of marking 166 at 5 mm increments to control the depth of insertion of the trephine into the disc space, as shown in FIG. 17. The markings 166 are compared to the working trocar 147 to gauge the depth of the cutting edge of the trephine, and therefore the depth of the prepared bore in the disc space and vertebral endplates. Again, the T-handle of the trephine allows the surgeon to rotate the trephine 165. This procedure is repeated at both of the electrocautery marks ML and MR. At this point, the surgeon has two bilateral holes to use for orientation during the remainder of the procedure. The trephine 165 is also preferably used to core into the disc space to form bilateral bores. A rongeur may be used to clear disc material from each of the bilateral bores in the disc.

In accordance with further steps of the present inventive method, a distractor 167 is advanced through the working trocar 147 as shown in FIG. 18. The distractor has a distractor tip 169 that is selected according to the vertebral level being instrumented. For instance, distractors for a 16 mm size implant can be either 12 mm or 14 mm in width to maintain the disc space at its proper anatomical height. The tip 169 is removably attached to a distractor shaft 168. Preferably, progressively larger distractor tips are sequentially inserted in alternating fashion into each of the bilateral holes in the disc space and annulus until the annulus is taut and the adjacent vertebrae are adequately distracted for restoration of a proper disc space height. In one aspect of the invention, the distractor tips 169, once they are disposed in their bilateral positions, will acts as a centering point or alignment guide for use of the instruments throughout the remainder of the procedure. It is therefore important that the distractor tips 169 be properly located, which can be accurately confirmed with fluoroscopy.

Figure 19:
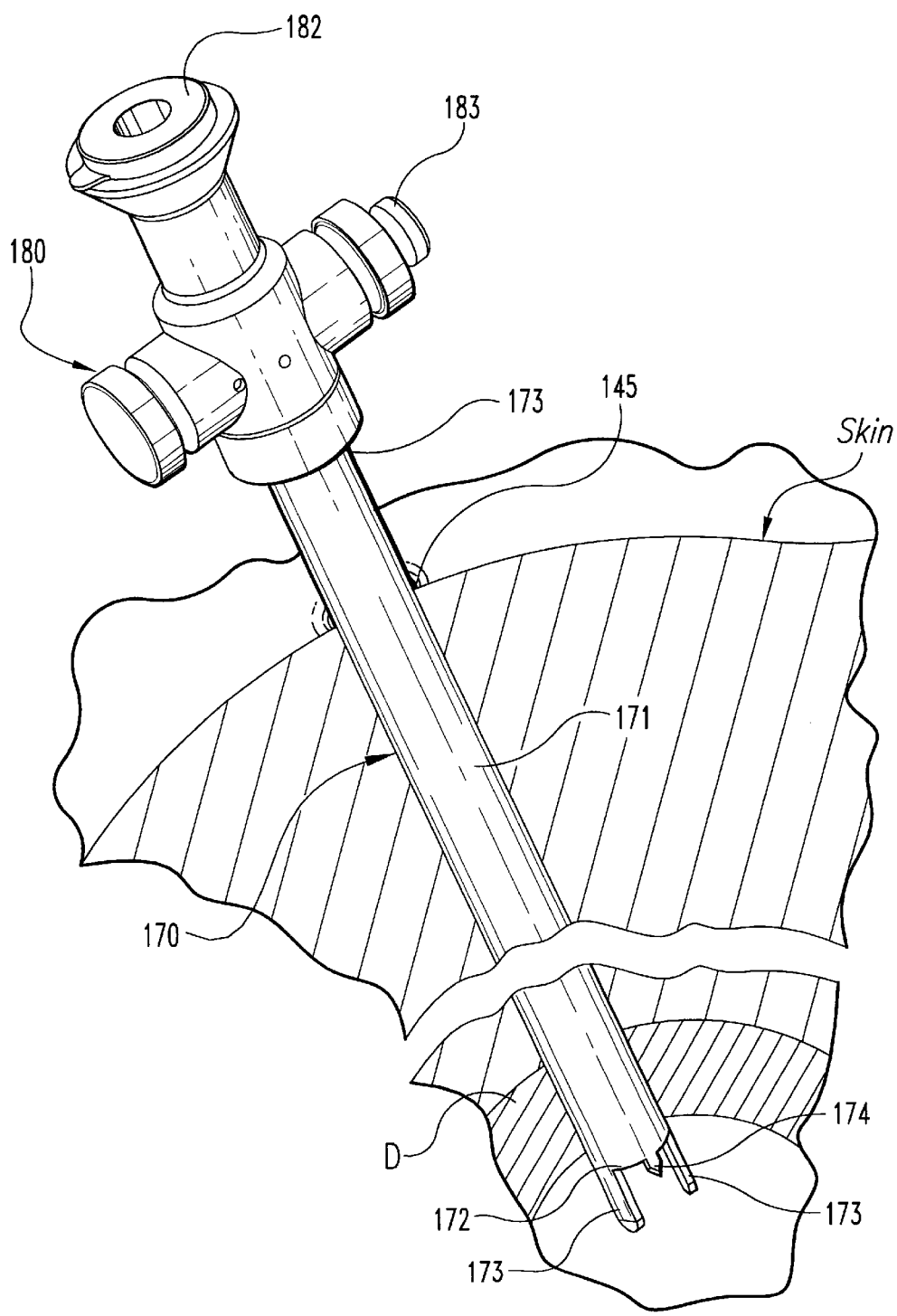
FIG. 19 is a perspective representation of the laparoscope according to the present invention in which the outer sleeve of the laparoscope is engaged within the subject disc space.

Once the bilateral distractor tips have been properly seated, a shaft extension (not shown) can be engaged to distractor shaft 168. At this point, in accordance with the preferred embodiment, the disposable trocar 147 is removed and a laparoscope 170 is introduced through the port 145 in the skin and into the disc space, using the distractor shaft and distractor tip as a positioning guide. In accordance with one embodiment of the present invention, the laparoscope 170 includes an outer sleeve 171 having a first end 172 and a second end 173, as shown in FIG. 19. The second end 173 is engaged to a laparoscopic port 180 which can be of conventional design. In particular, the laparoscopic port 180 can include a bore 184 (FIG. 20(*a*)) extending therethrough and in communication with the interior of the hollow outer sleeve 171. This bore 184 in the laparoscopic port allows introduction of instruments through the port and into the outer sleeve 171. The bore is preferably closed by a number of seals 182, which are configured to accept cylindrical tools and instruments therethrough while maintaining tight sealed engagement about the instrument.

The laparoscopic port 180 also preferably includes a trumpet valve 183, which can be of conventional design. Specifically, the trumpet valve 183 maintains the laparoscopic port 180 in a normally closed position in which its internal bore is closed from communication with the outer sleeve 171. However, once a instrument is introduced into the port 180 through the seals 182, the trumpet valve 183 moves aside to allow passage of the instrument or tool into the sleeve 171.

In a further unique aspect of the invention, the end 172 of the outer sleeve 171 includes a pair of opposite distraction extensions or fingers 173. These distraction fingers 173 are sized according to the height of the particular disc space. Specifically, the fingers 173 are intended to maintain the spacing between the adjacent vertebrae during subsequent steps of the procedure after the distractor tip 169 has been removed. Thus, the width of the fingers 173 can be varied depending upon the particular vertebral level being instrumented. In addition, the distraction fingers 173 can be tapered to conform to a normal angle between adjacent vertebrae at the instrumented level. The position of the fingers 713 is correlated with the position of the distractor tips within the bilateral bores in the disc space by aligning the fingers 173 with the trumpet valve 183 when the port 180 is engaged to the outer sleeve 171. When the laparoscope 170 is inserted, the trumpet valves provide a visual indication of the alignment of the fingers. In other words, when the trumpet valve 183 is lateral to the midline, the fingers 173 are properly oriented between the vertebral endplates.

In one specific embodiment, the outer sleeve 171 can include opposite spikes 174 disposed between the distraction fingers 173. These spikes are preferably configured to penetrate at least partially into the adjacent vertebral bodies, to help maintain the position of the outer sleeve 171 at the surgical site. In some instances, the outer sleeve 171 does not include the teeth 174. For example, where the procedure is to implant a tapered fusion device, the teeth 174 are preferably eliminated and where the device is a uniform cylinder, the teeth can be retained.

Figures 20A, 20B:
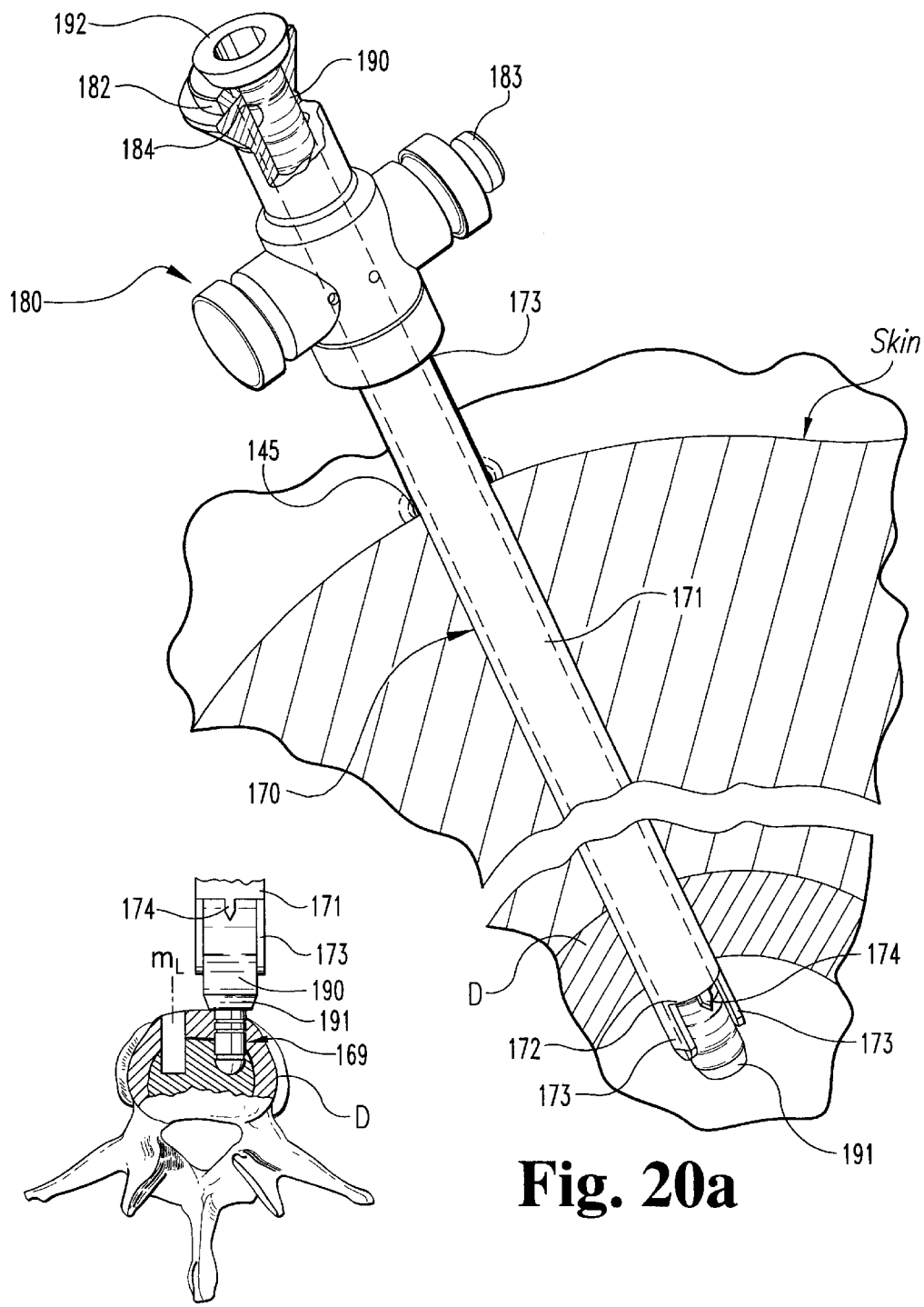
FIG. 20(a) is a perspective representation of the laparoscope of FIG. 19 with a switching sleeve according to one aspect of the invention disposed within the laparoscope.
FIG. 20(b) is an enlarged A-P representation of the laparoscope and switching sleeve of FIG. 20(a) showing the positioning of the distractor tip as depicted in FIG. 18.

In one embodiment of the present surgical method, the laparoscope 170 can be directly inserted over the distractor shaft extension (not shown). However, it is believed that the distraction fingers 173 and the spikes 172 can cause trauma to the skin during entry and to the soft tissue surrounding the surgical site during introduction of the laparoscope 170. Thus, a further feature of the preferred embodiment includes a switching sleeve 190, as shown in FIGS. 20(a), (b). The switching sleeve 190 has a length sufficient to span the entire length of the laparoscope 170 from the port seals 182 to the end 172 of the outer sleeve 171. In particular, the switching sleeve 190 has a tapered tip 191 configured to extend beyond the end 172 of the outer sleeve 171, and more particularly beyond the ends of the fingers 173. The switching sleeve 190 also includes a flared tip 192 at its opposite end that is enlarged to prevent its passage through the laparoscopic port 180 and particularly the seals 182.

In accordance with a preferred embodiment of the inventive surgical procedure, the switching sleeve 190 is placed inside the laparoscope 170 prior to insertion into the patient. The switching sleeve 190 has an outer diameter nearly equal to the inner diameter of the outer sleeve 171 to slide in close running fit within the laparoscope 170. The laparoscope 170 and switching sleeve 190 can then be slide over the distractor shaft and with a twisting motion pass through the skin and fascia until the outer sleeve contacts the disc annulus. It is important to consider that the opposite fingers 173 on the outer sleeve 171 of the laparoscope must pass through the opening in the disc space and be aligned between the adjacent vertebrae. As the fingers 173 are pushed into the disc space, the switching sleeve 190 will remain outside the disc annulus as its tapered tip 191 contacts the annulus in the region between the distraction fingers 173 (see FIG. 20(b)). The outer sleeve 171 of the laparoscope 170 is properly oriented when the fingers 173 are correctly oriented between and contacting the adjacent vertebra endplates. The outer sleeve 171 is then seated by striking a driving cap (not shown) mounted on the laparoscopic port, to thereby drive the fingers 173 fully into the disc space between the vertebral endplates and to drive the spikes 174 into the adjacent vertebrae.

With the laparoscope 170 in place, all of the remaining steps of this inventive technique occur under a relatively protected or sealed environment. Specifically, the outer sleeve 171 of the laparoscope provides a sealed passageway from the bilateral bores at locations MR and ML on the disc to the laparoscopic port 180 outside the patient. The laparoscope 170 can be used as a passageway to provide irrigation and aspiration where necessary, without the risk of fluids leaking into the space adjacent the operative site. Moreover, the sealed working channel to the prepared sites in the disc space prevent leakage of abdominal distension fluids into the working channel and disc space. This latter aspect allows direct vision of the surgical site outside the working channel created by the laparoscope.

With the laparoscope 170 in position, the distractor shaft 168 is removed as well as the distractor tip 169 that is disposed between the adjacent vertebrae. Since the fingers 173 of the laparoscope outer sleeve 171 will maintain the spacing between the adjacent vertebrae, the distractor tip is being removed from the disc space to prevent dislodgment of the outer sleeve. In a bilateral procedure, the bilateral bores in the disc each contain a distractor tip. In the preferred method, the right left bore remains in place. Thus, the fingers 173 of the laparoscope engaged within one of the bilateral locations share the distraction load with a distractor tip 169 disposed within the other bilateral location. When the right side is instrumented with a fusion device, as described below, the fingers 173 will be within the left bore in the disc and will share the distraction load with the fusion device.

Figure 21:
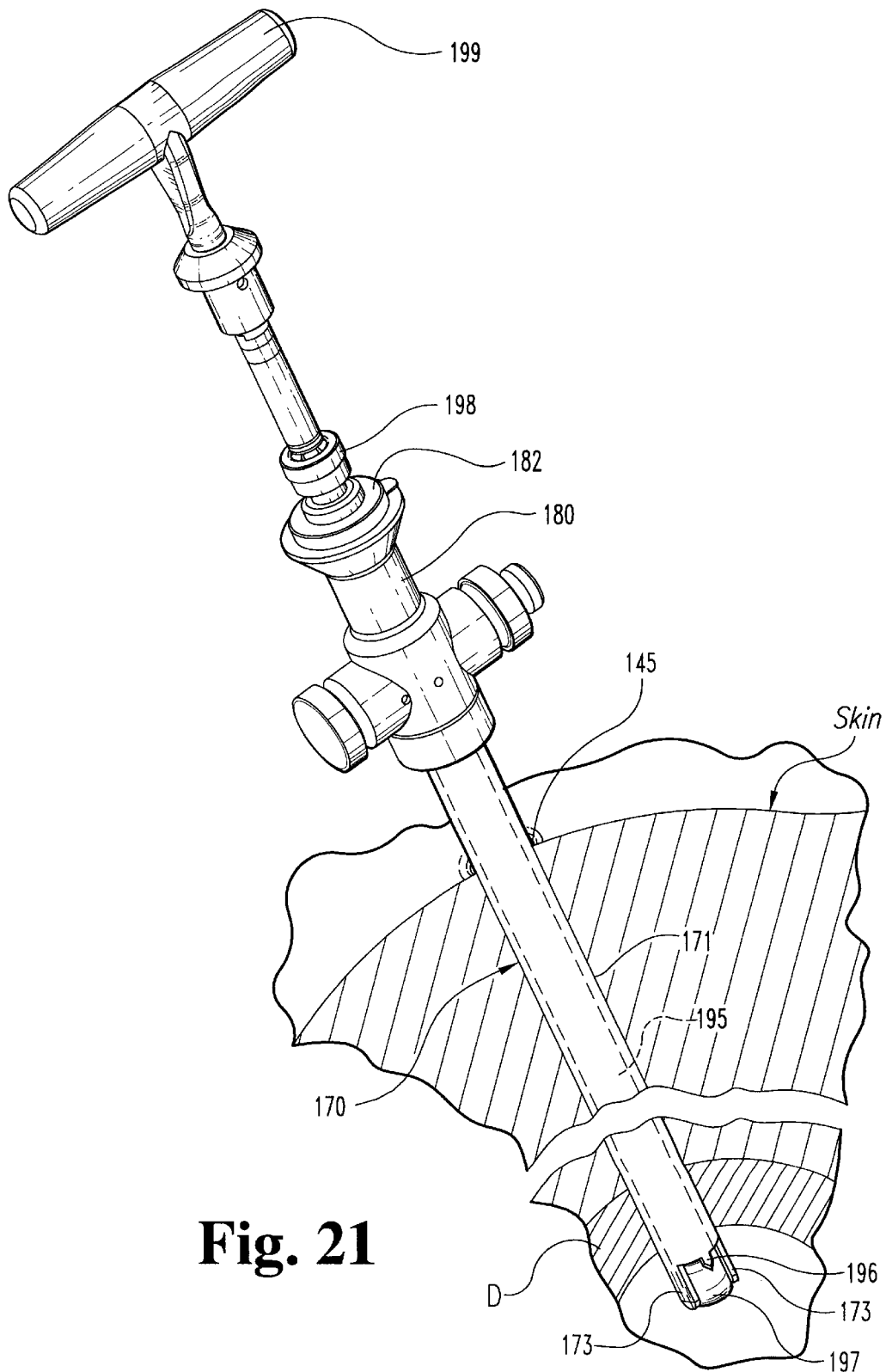
FIG. 21 is a perspective representation of the laparoscope of FIG. 19 with a reamer extending through the laparoscope to prepare the site for receiving a fusion device.

With the distraction tip removed and the disc space supported by the fingers 173, the next step in the inventive method is the preparation of the vertebral end plates and disc to provide a site for insertion of a fusion device. The switching sleeve 190 is first removed and, in accordance with one aspect of the invention, a reaming sleeve 195 is advanced through the laparoscope 170. As shown in FIG. 21, the reaming sleeve 195 includes spikes 196 that are adapted to penetrate the adjacent vertebral bodies to hold the reaming sleeve in place. One object of the reaming sleeve in this embodiment is to help maintain the position of the laparoscope while the disc material and vertebral end plates are being reamed. This object is of particular importance when the laparoscope outer sleeve 171 does not include the teeth 174. In addition, the spikes 195 on the reaming sleeve 195 will prevent the vertebral bodies from being pushed away or distracted while reaming, since the force generated by the reamer can have a tendency to drive the vertebral bodies apart. This force is particularly present when a tapered fusion device is to be implanted, necessitating cutting conical threads into the vertebra.

In accordance with the invention, an adjustable reamer 197 is extended through the reaming sleeve 195. The reamer 197 can be of conventional design with a cutting surface configured to evacuate the disc space and prepare the adjacent vertebral bodies to receive a threaded implant. The reamer 197 includes an adjustable depth stop 198 disposed adjacent the laparoscopic port 180. The depth stop 198 contacts the seals 182 of the port to prevent introduction of the reamer 197 to deeply into the disc space. The depth of reaming necessary, and consequently the position of the depth stop 198, can be determined prior to this reaming step by review of fluoroscopic images.

The reamer 197 is manually operated by way of a T-handle 199 to successively remove disc tissue and bone from the adjacent vertebral bodies to provide a prepared bore for the fusion implant. Preferably, several passes will be made with the reamer, after which the outer sleeve will be examined visually and fluoroscopically to verify that it remains fully seated within the disc space. In addition, the reaming should be observed under C-arm imaging to prevent reaming into the spinal canal. Preferably, the depth stop 198 will be set at an initial drilling depth less than the anticipated full depth for implant insertion. For example, for an L5–S1 fusion, a 20 mm deep reamed bore may be prepared for a 26 mm long implant.

After the disc material and vertebral bodies have been reamed by the reamer 197, one prepared site is available for insertion of the fusion implant at the right location MR. It is then necessary to prepare the other bilateral location previously marked using the template 150 (location ML in FIG. 15). In the next steps of the inventive method, the reamer 197 is withdrawn as well as the reaming sleeve 195. The laparoscope 170 is then unseated in a controlled manner so that the fingers 174 are disengaged from between the vertebrae and withdrawn through the opening of the disc annulus. However, the laparoscope 170, and particularly the outer sleeve 171, is not removed from the skin after unseating from the disc space. Instead, the outer sleeve is reoriented over the second bilateral location ML (see FIG. 15). Preferably, immediately after the outer sleeve 171 is disengaged from the disc annulus, the switching sleeve 190 is extended back through the outer sleeve 171 so that the tapered end 191 of the sleeve extends beyond the fingers 173. The switching sleeve will then protect the soft tissue surrounding the instrumented disc space as the outer sleeve 171 is repositioned over the second bilateral location ML.

With the laparoscope 170 oriented over the second location ML and with the switching sleeve 190 contacting the disc annulus, a distractor tip 169 attached to a distractor shaft 168 is extended through the outer sleeve 171. In the preferred technique, the laparoscope is not yet fully seated at this location ML. The distractor tip 169 is advanced through the bore within the disc and anchored between the adjacent vertebral end plates. The laparoscope 170, and particularly the outer sleeve 171, is reseated within the disc space in the manner described above, namely with the distraction fingers 173 disposed between the vertebral end plates. Once the position of the outer sleeve and fingers 173 is confirmed using fluoroscopy, the remaining steps for preparing the vertebral bodies to receive the fusion implant are repeated at the left location ML.

Figure 22:
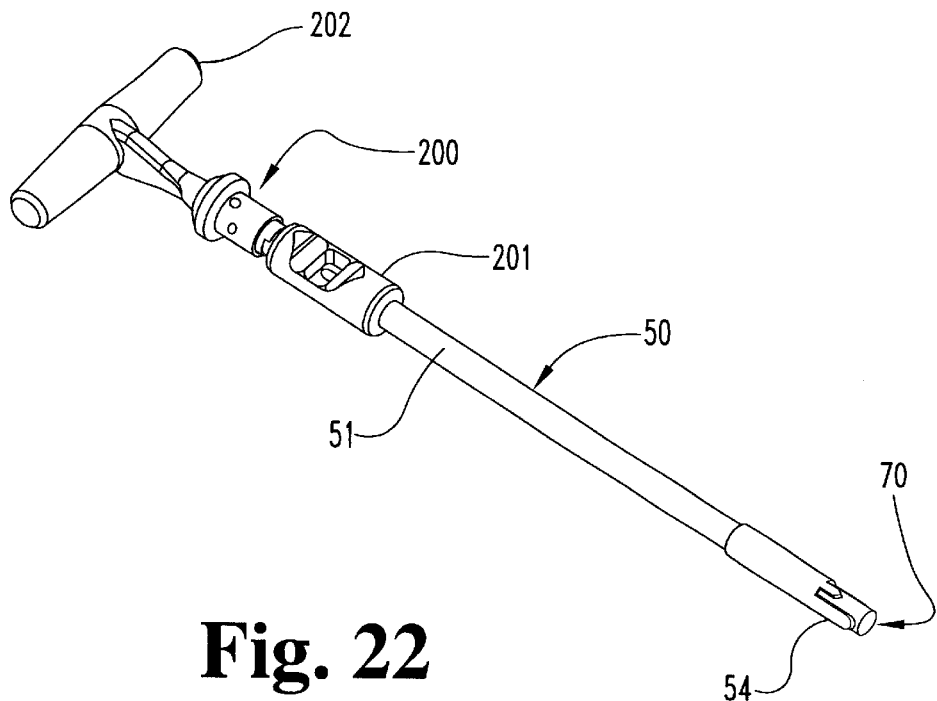
FIG. 22 is a perspective view of an implant driver of the type shown in FIG. 2 engaged to a fusion device and including a T-handle assembly engaged to the driver.

Once the second bore in the disc space has been prepared, the following steps of the technique involve insertion of the implant. In accordance with the present invention, the implant can be a fusion cage of the type shown in FIG. 1 which is tapered to restore the normal curvature at the particular vertebral level. In the case of a fusion cage of the type shown in FIG. 1, the implant driver 50 can be used to implant the device 10. The implant drive 50 can be substantially as depicted in FIG. 2 and can engage the implant 10 as shown in FIG. 3. In accordance with the present technique, the implant drive 50 can be engaged by a T-handle assembly 200, as shown in FIG. 22. The T-handle assembly 200 includes a collet 201 which engages the end of the implant drive 50 opposite the gripping tongs 54. The assembly 200 also includes T-handle 202 which is aligned with the gripping tongs 54 so that the surgeon has a visual indication of the orientation of the tongs 54 when the implant driver 560 is extended through the laparoscope 170.

In accordance with the preferred technique, the implant drive 50 carrying the fusion device 10 is inserted through the laparoscopic port 180 and through the outer sleeve 171 until the implant 10 contacts the prepared bore within the disc space. At that point, the implant drive 50 can be rotated using the T-handle 202 to thread the implant into the prepared bore. The implant driver 50 can preferably include a plurality of depth markings on the driver shaft 51 beneath the collet 201 to give the surgeon the visual indication of the depth of insertion of the implant 10 into the prepared bore. Once the implant has been screwed in to its predetermined depth, as indicated by the depth markings on the implant drive shaft 51, insertion of the implant should be halted with the T-handle 202 parallel to the vertebral end plates. With this orientation of the T-handle 202, the tongs 54 of the implant drive 50 will be exposed to the disc space, rather than in contact with the vertebral bone. Consequently, then the long slots 27 (see FIG. 1) of the fusion device 10 will be directly exposed to and in contact with the vertebral bodies.

With a fusion device 10 implanted within the left location ML, the implant driver is removed from the implant and the laparoscope 170 is unseated from the left bilateral location. Again, the laparoscope 170 is not removed from the skin after unseating, but is simply moved to the next bilateral location MR, preferably with the switching sleeve 190 protecting the surrounding tissue from the distraction fingers 173 of the laparoscope. At this location, the same steps are repeated to implant a second fusion device 10 at this right location.

When each of the implant devices 10 is bilaterally implanted within the disc space, the position of the implants should be confirmed. In some instances, it may be necessary to reposition an implant within the disc space, such as by driving it further into the disc space. In this instance, the driving attachment 120 can be engaged to the implant drive 50 and the attachment 120 engaged with the implanted device 10 to permit additional manipulation of the device.

In switching between the left location RL and the right location MR, it is preferred that the implant drive 50 be fully removed from the laparoscope 170 and the switching sleeve 190 extended through the outer sleeve 171. Also, the distractor tip 169 attached to the distractor shaft 168 should then be extended through the switching sleeve 170 and the distractor tip can be used to locate the previous bore at the right location MR. Once the distractor tip 169 is situated within the bore, the outer sleeve 171 can be seated at the right most location in the disc space. With the outer sleeve 171 properly seated, the distractor shaft can be removed to make way for the implant drive 50 carrying a new implant fusion device 10. Of course, the switching sleeve is removed prior to extending the implant and implant drive through the outer sleeve 171.

Once both fusion devices are disposed in their bilateral positions at location ML and MR, an A-P radiograph can be taken to assure proper placement. In addition, where possible, it is preferred that additional bone graft material is packed around the implants in situ to further facilitate fusion.

As discussed above, the fusion device 10 includes a hollow opening 15 to receive bone growth material. In one specific embodiment, this bone growth material can include autogenous bone harvested from the patient's anterior iliac crest. Autograft bone from other locations, autologous bone, allograft, bone growth substitutes or other bone material capable of promoting or inducing bone ingrowth can be loaded into the implant. In the preferred technique, the interior 15 of each fusion implant 10 is filled prior to insertion of the implant into the disc space.

Figure 23:
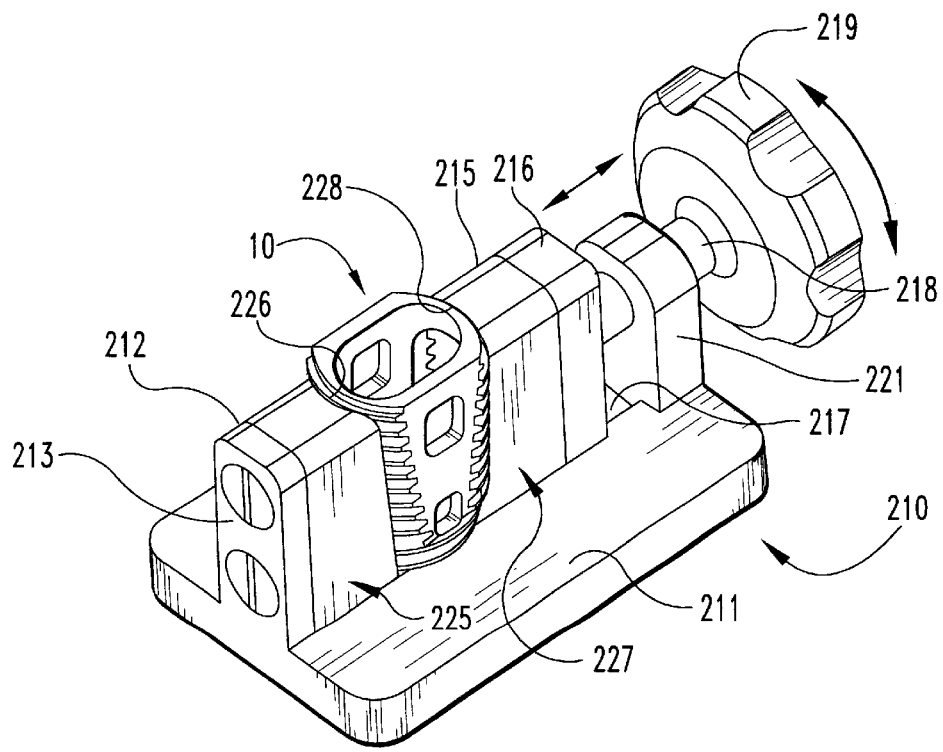
FIG. 23 is a perspective view of an implant holder according to one aspect of the present invention.

The facilitate this "pre-loading" of the fusion material, an implant holder 210 is provided in accordance with the invention (FIG. 23). This holder 210 includes a base 211 that includes a fixed clamp section 212 and a movable clamp section 215. The fixed clamp section 212 includes a flange 213 projecting from the base 211. The movable clamp section includes an impactor plate 216 that slides within a groove 217 formed in the base 211. The impactor plate 216 is connected by a threaded shaft 218 to a knob 219. The threaded shaft is rotationally supported by an upstanding flange 221 attached to base 211. The upstanding flange 221 includes a threaded bore (not shown) through which the threaded shaft 218 extends. As the knob 219 is rotated, the shaft rotates within the threaded bore of the flange 221 to move the impactor plate 216 forward toward the fixed clamp half 212.

In accordance with the present embodiment, a pair of blocks 225 and 226 are provided which are disposed adjacent a corresponding one of clamp sections 212 and 215. The blocks 225 and 227 include implant engagement surfaces 226 and 228 which are configured to match the outer shape of the implant at its large slots 27. These blocks, therefore, serve to close off the slots 27 as bone growth material is packed into the opening 15 of the implant 10. In one specific embodiment, the blocks 225 and 227 are formed of plastic to effectively seal the large openings 27 in the sides of the implant 10. Once the bone growth material has been tightly compacted within the implant device 10, the knob 219 can be rotated in the opposite direction to release the movable clamp 216 from the device 10.

Figure 24:
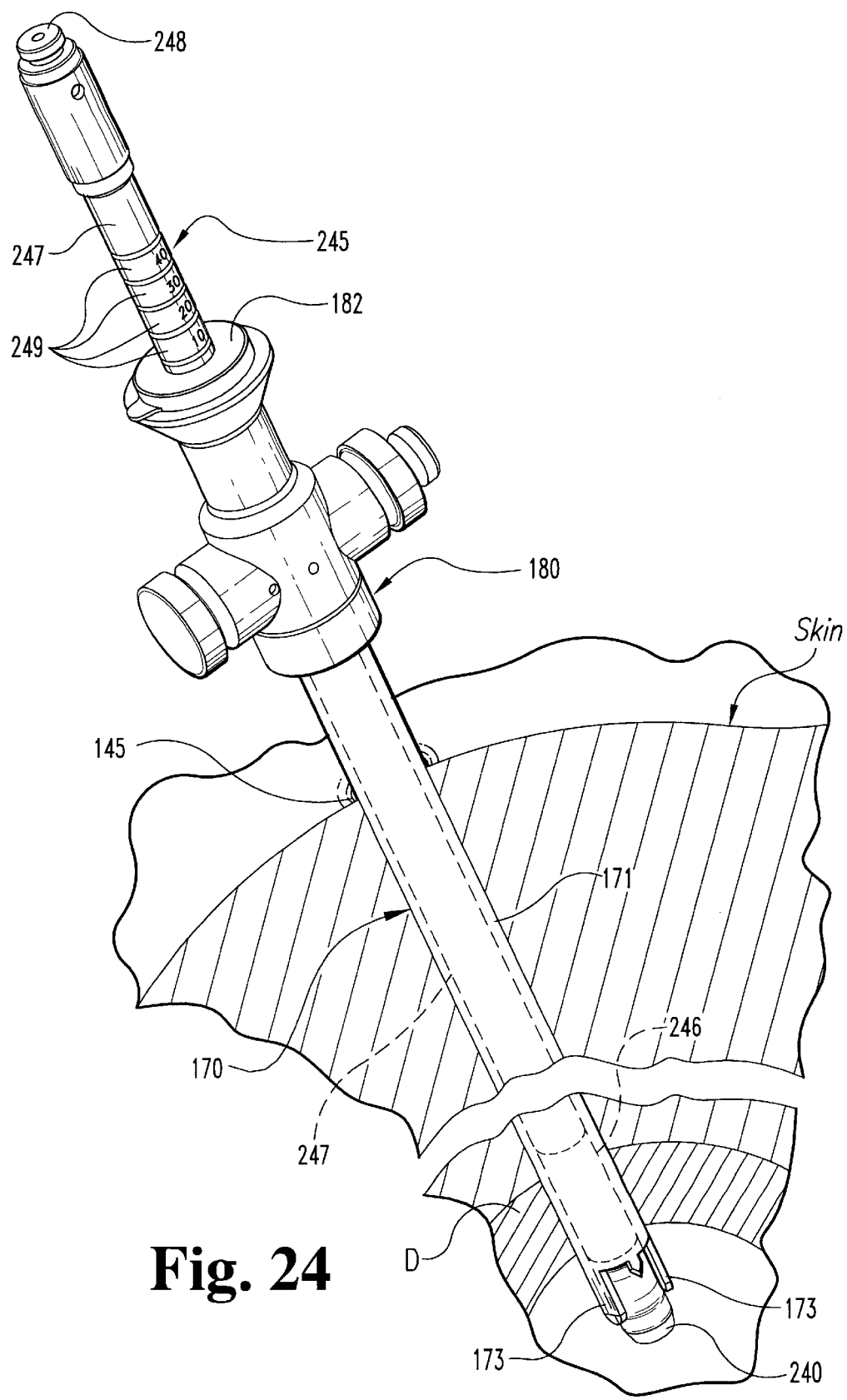
FIG. 24 is a perspective representation of the laparoscope used to implant a bone dowel within the prepared site and including a bone dowel impactor in accordance with one aspect of the present invention.

In accordance with another aspect of the present invention, the laparoscope 170 can be used to implant a bone dowel 240, as depicted in FIG. 24. The bone dowel 240 can be of a variety of configurations, such as an allograft Crock dowel, autograft tricortical or button dowels, manufactured composite dowels or hybrid dowels (e.g., an autogeneous button combined with allograft Crock dowel). While it is preferable that the bone dowel 240 be cylindrical, this configuration is not essential to the invention, provided the dowel is configured to pass easily through the outer sleeve 171 of the laparoscope.

In accordance with this embodiments, the disc space and adjacent vertebral bodies are prepared as described above (see, FIGS. 13–21 and accompanying text). In the preferred technique for implanting a bone dowel, the reamer 197 is used to create a partially cylindrical cut in the vertebral endplates to receive a cylindrical dowel. Alternatively, if a non-cylindrical dowel is used, the endplates can be prepared accordingly. It is understood that the dowel will typically have a uniform outer diameter or width corresponding to the disc space height. Unlike the fusion device 10 discussed above the bone dowel is not tapered; however, preparation of the vertebral bodies with the tapered distraction fingers 173 of the outer sleeve 171 providing an appropriate angle will allow the implanted bone dowel to retain this angle.

Once the disc space and vertebral endplates have been prepared to receive the dowel, the bone dowel 240 is dropped into the laparoscope through outer sleeve 171. Due to the precise fit between the bone dowel and the vertebral endplates, resistance will be experienced during insertion of the dowel. An impactor 245 is provided to drive the dowel into its prepared site. The impactor includes an impactor head 246 that is preferably threaded engaged to an impactor shaft 247. The head and shaft are sized for a close running fit through the outer sleeve 171. Preferably, the impactor head 246 can be provided to be implanted. Also preferably, the impactor shaft 247 will have a smaller diameter so that it can be used with impactor heads and outer sleeves of several diameters.

The impactor shaft 247 includes a driving cap 248 that can be stricken by a hammer or similar tool to drive the bone dowel into the prepared site in a controlled manner. Preferably, the impactor shaft also includes a series of depth markings 249 corresponding to the depth of insertion of the bone dowel 240 into the disc space. The final position of the dowel can be verified later by A-P radiograph. The second bone dowel can be inserted in a similar manner and additional bone graft placed between the bilateral bone dowels.

The present invention involves instruments and surgical techniques usable at any level of the spine. For simplicity, the above discussion has focused on fusion of the L5–S1 disc space. The dimensions of each of the components of the instruments would be sized appropriately for the specific vertebral level being instrumented. For example, the fusion devices 10 may be offered in several sizes, including 12 nm, 14 mm, and 16 mm. Based upon the size of the fusion implant, the trephine 165 can be provided in several sizes, such as trephines to form bores having a diameter of 6 mm, 8 mm or 10 mm.

The distractor tips 169 are also sized according to the size of the fusion device to be implanted. Preferably, the distractors are smaller than the fusion device. For example, for a 16 mm fusion device, the distractor tips 169 can be either 12 mm or 14 mm. For a 16 mm fusion device, a 16 mm reaming sleeve is provided to accept a 16 mm reamer to prepare a hole of the same diameter within the disc space and vertebral bodies. Smaller reamers and reaming sleeves would be provided for smaller fusion devices. As previously described, the outer sleeve 171 of the laparoscope 170 is preferably a 2 mm in diameter to readily accept all of the instruments and sleeves passing therethrough during the several steps of the inventive procedure.

In the surgical techniques described above in relation to FIGS. 13–21, an outer sleeve 171 is utilized which incorporated fingers 173 that served to maintain distraction of the intervertebral space. In addition, the prior illustrated technique utilizes a series of distractor tips 169 that are used to maintain distraction at one side of the disc space while a fusion device is implanted in the other bilateral location. A further embodiment of the present invention provides an improvement to this technique. Specifically, this improvement resides in a distraction mechanism that is centrally disposed between the bilateral fusion device locations. This centralized distraction provides a more uniform distraction across the entire disc space than can be provided by a distractor tip, such as tip 169, situated at one side or the other of the intervertebral space.

In accordance with the embodiment of the invention shown in FIGS. 25–27, a distractor plug 290 is provided that includes an elongated stem 291 terminating at one end in a fan-shaped flange 292. The stem is sized to be maintained within the disc space. In one specific embodiment, the stem 291 has a length of about 22 mm. The flange 292 includes a forward facing bone contacting face 293 that is adapted to contact the vertebral bone in a manner disclosed herein. The elongated stem 191 includes opposite inwardly curved or concave walls 194. The curved walls 194 of the stem 191 merge into or are contiguous with opposite curved or concave edges 195 of the flange 192. In accordance with the present invention, these curved walls 294 and curved edges 295 are preferably sized to provide clearance for the outer diameter of various tools and instruments that might be advanced into the intervertebral disc space through an outer sleeve, such as the sleeve 171 described above. In a specific embodiment, these contiguous curved walls 194 and edges 195 are defined at a diameter of between 20 mm–29 mm.

The distractor plug 290 further includes a locking surface 297 at the top and bottom portions of the elongated stem 291 and intermediate between the opposite curved walls 294. These locking surfaces 297 can have a variety of configurations; however, in one specific embodiment, these locking surfaces 297 includes a series of ridges 298 that are adapted to provide a modest grip on the endplates of the adjacent vertebrae that will contact the elongated stem 291 of the distractor plug 290. In accordance with the invention, the elongated stem 291 has a height between the two locking surfaces 297 that approximates the distracted height of the disc space to be instrumented. In the case of a threaded fusion device, such as the device 250, this height of the elongated stem 291 will be less than the outer crest diameter of the threads of the fusion device 250. In a specific embodiment, the top and bottom locking surfaces 297 define an outer diameter of between 10 mm–14 mm.

The distractor sleeve 290 further includes a lower stop face 296 that is integral with the flange 292 but that is on the opposite side of the elongated stem 291 from the bone contacting face 293. The elongated stem 291 is hollow with a bore extending along its length, as shown in FIG. 26. The stem 291 defines a threaded bore 302 at the end adjacent the flange 292. The threaded bore merges into and communicates with a keyed bore 301 that is at the opposite end of the distractor plug 290. The opposite end of the stem 291 of the plug 290 forms a blunt nose 299 through which the keyed bore 301 exits. In the illustrated embodiment, the keyed bore 301 is square in configuration. Alternatively, the keyed bore can have a variety of shapes that permit a keyed interface with a similarly shaped spike extending through the bore 301.

In its use, the distractor plug 290 is configured to be pushed into the intervertebral disc space between adjacent vertebrae. The distractor plug 290 is particularly well suited to providing distraction in a disc space spanning a spondylolisthesis condition. In this condition, one of the vertebrae is anteriorly offset from an adjacent vertebrae. In the condition specifically illustrated in FIG. 28, the superior lower lumbar vertebrae L5 is offset from the inferior sacral vertebra S1. Thus, the distractor plug 290 is advanced anteriorly into the disc space between the lumbar vertebra L5 and sacrum S1.

The blunt nose 299 first contacts the adjacent vertebrae and provides a smooth and steady distraction as the remainder of the plug, namely the elongated stem 291, comes in contact with the endplates of the adjacent vertebrae. In order to drive the distractor plug 290 into this disc space, the present invention contemplates a plug driver 305. While the plug driver 305 can have a variety of configurations, in its simplest form the driver 305 includes a threaded stem 306 projecting from an elongated bar 307. A handle 308 is formed at an opposite end of the bar 307 to provide a gripping surface to push the plug driver 305 toward the instrumented disc space. The threaded stem 306 of the plug driver 305 is configured to engage the threaded bore 302 of the distractor plug 290. Thus, the distractor plug 290 is first threaded onto the end of the plug driver 305 and then subsequently advanced anteriorly into the disc space between the adjacent vertebrae.

As a force F is applied to the distractor plug 290 through the plug driver 305, the flange 292 is advanced toward the lumbar vertebra L5 until the bone contacting face 293 is in contact with the vertebra. At this point, further force F applied to the distractor plug 290 not only pushes the elongated stem 291 into the intervertebral space, but also pushes the lumbar vertebra L5 into its proper alignment with the sacrum S1.

As the distractor plug 290 is advanced further into the intervertebral space, the upper and lower locking surfaces 297, and particularly the ridges 298, grip the adjacent vertebral endplates to prevent retrograde expulsion of the distractor plug 290. The locking surfaces 297 of the distractor plug 290 provide a sufficiently strong engagement between the vertebral endplates to also prevent restoration of the original spondylolisthesis condition. The distractor plug 290 is pushed further into the intervertebral space until the stop face 296 of the flange 292 contacts the inferior vertebra, in this case the sacrum S1. It is understood that this stop face 296 can have a variety of configurations depending upon the desired final orientation of the two vertebrae relative to each other. For instance, the flange 292 can be wider at the stop face 296 than at the bone contacting face 292 so that the anterior portion of the displaced vertebra still retains some anterior offset from the anterior portion of the properly positioned vertebra.

It is known that some threaded cages can permit a reduction of a spondylolisthesis condition, provided the condition is only a grade one. The distractor plug 290, and particularly the locking surface 297 of the stem 291 and the flange 292, permit reduction of higher grade spondylolisthesis conditions. The flange and locking surfaces reduce the risk of slippage between the inferior and superior vertebrae as the superior vertebra is reduced.

In an alternative embodiment, a distractor plug 310 is provided that does not include a flange, as in the case of the distractor plug 290 shown in FIG. 25. Specifically, the distractor plug 310 shown in FIG. 20 includes an opposite curved or concave sidewall 311, a blunt nose 312 and opposite locking surface 313. Each of these features is substantially similar to the features of the distractor plug 290. Likewise, the distractor plug 310 includes a stop face 314 that is adapted to contact the inferior vertebra during the reduction process. Finally, the distractor plug 310 is hollow and includes a threaded bore (not shown) and an integral keyed bore 315.

With this embodiment, the primary reduction force is provided by the driver 316, depicted in FIG. 30. This driver includes a threaded stem 317 that is adapted to engage the threaded bore (not shown) in the distractor plug 310 of FIG. 29. A driving flange 318 is formed so that the threaded stem projects outward from the driving flange 318. The driving flange 318 includes a bone contacting surface 319 that at least initially contacts only the end of the distractor plug 310 when the stem 317 is threaded into the plug. Once the driver 316 is used to push the distractor plug 310 in place, the bone contacting face 319 abuts the displaced vertebra and is used to transmit a force to reduce that vertebra.

Figure 31:
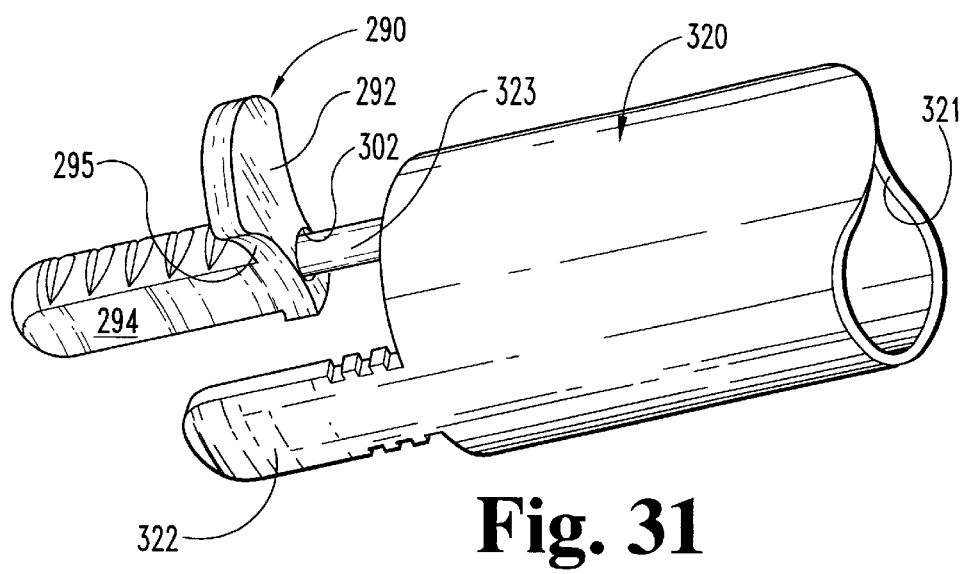
FIG. 31 is a rear perspective view of a percutaneous surgical sleeve in engagement with a distractor plug in accordance with the embodiment shown in FIG. 25.

As described above, the distractor plugs 290 and 310 first provide a means for reducing a spondylolisthesis condition. Once the vertebral offset has been reduced, the driving tools can be removed and the distractor plugs 290, 310 left in position in the intervertebral disc space. At this point, a further feature of the distractor plugs comes into play. Specifically looking, for example, at the distractor plug 290, the hollow stem 291, and particularly the keyed bore 301 provides an interface for a percutaneous surgical sleeve. In one embodiment, such a sleeve 320 includes a tubular body 321 as shown in FIG. 31. A distraction extension 322 is formed at one end of the tubular body 321. This distraction extension preferably has a height that is comparable to the height of the elongated stem 291 so that the extension can assist in maintaining the distracted height of the intervertebral space.

Substantially 180 degrees diametrically or laterally opposite from the distraction extension 322 is a locating spike 323. In the specific embodiment, the locating spike 323 integrally extends from the end of the tubular body 321 contiguous with the outer wall of the body. This locating spike 323 is configured to extend first through the threaded bore 302 and finally through the keyed bore 301 of the distractor plug 290. The locating spike 323 preferably has a shape that conforms to the shape of the keyed bore 301. In the specific embodiment, that shape is a square, although other configurations can be utilized that prevent relative rotation between the distractor plug 290 and the locating spike 323. The locating spike is preferably long enough to extend through the entire stem 291 without projecting beyond the blunt end 299 of the distraction device.

Figure 32:
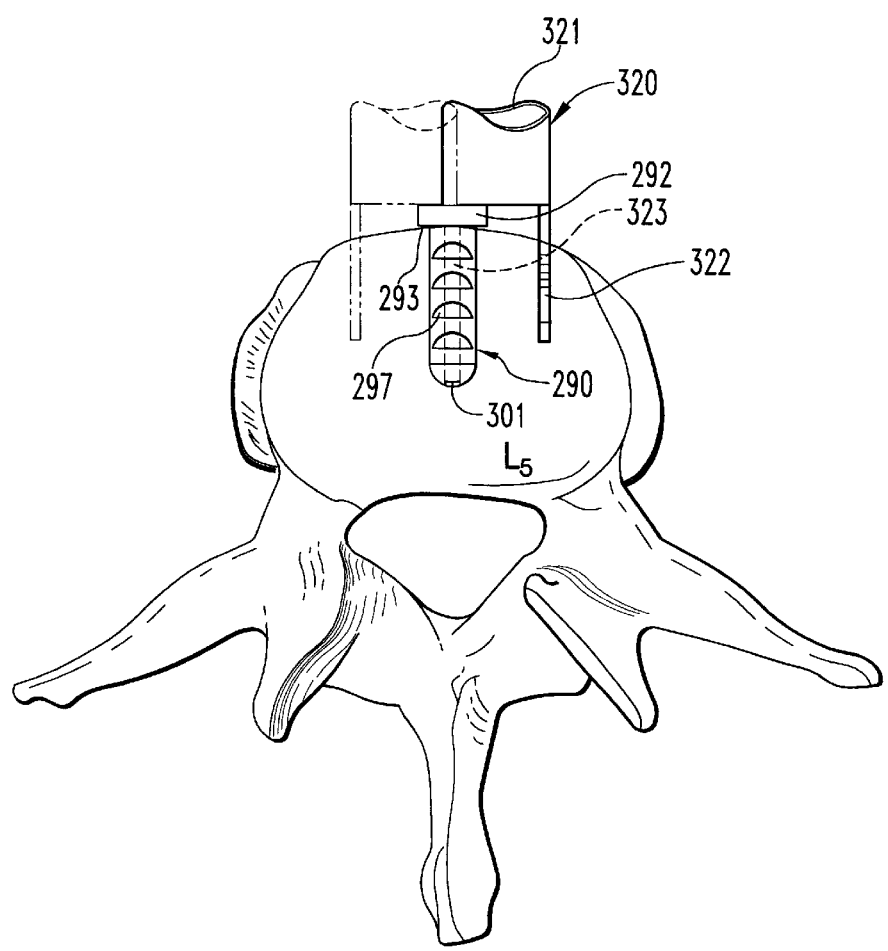
FIG. 32 is a superior A-P view of a vertebra of the spine with the distractor plug and percutaneous surgical sleeve shown in FIG. 31 disposed within the disc space, with an alternative position of the sleeve shown in phantom.

The manner of use of the distractor plug and sleeve combination is shown in FIG. 32. In particular, it can be seen that a distractor plug 290 is centrally located within the intervertebral disc space. The distractor plug 290 then serves as a locator or an anchor for the sleeve 320. Specifically, the locating spike 323 projects into the distractor plug 290 into keyed engagement with the keyed bore 301. As shown in FIG. 32, the sleeve 320 is oriented to the right of the centrally disposed distractor plug 290 so that the distraction extension 322 provides outboard support for the distracted disc space. In this position, the sleeve 320 can then be used to perform the drilling and reaming operations previously described particularly in connection with FIG. 21, as well as the step of inserting the fusion device as also described above. The curved wall 294 and curved edge 295 of the flange 292 provide clearance for insertion of the various cylindrical tools and cylindrical fusion device into the intervertebral space.

Once a fusion site has been prepared at the right side of the disc space, the sleeve 320 can be retracted, so that the locating spike 323 is pulled out of the keyed bore 301 of the distractor plug 290. The sleeve 320 can then be rotated to the position shown in phantom in FIG. 32 with the tubular body 321 directed to the left of the intervertebral disc space. The same operations can be performed at this location in the intervertebral space. Using the distractor plug 290 and the sleeve 320, the present invention provides a means to maintain midline distraction through the center line of the intervertebral disc space. Moreover, the distractor plug provides a constant fixed pivot point for the various operations involved in implanting an interbody fusion device.

Figure 33:
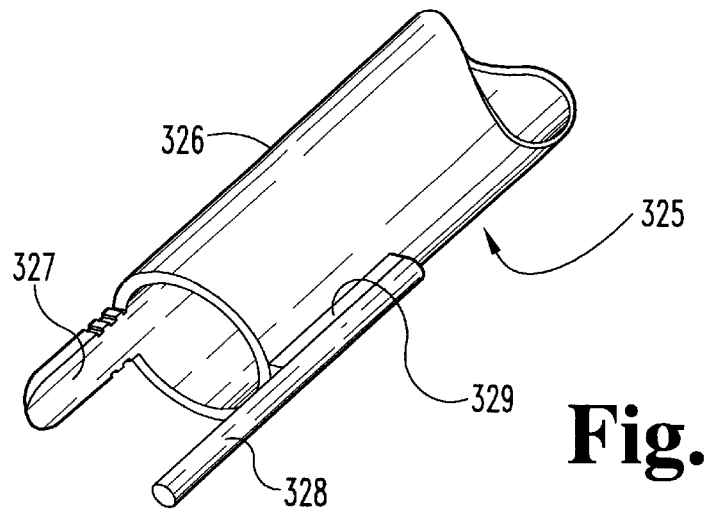
FIG. 33 is a side perspective view of a percutaneous surgical sleeve in accordance with a further embodiment of the invention with an outrigger spike engaged thereto for attachment to a distractor plug according to FIG. 25 or 29.

In accordance with another embodiment of the invention, a sleeve 325 is provided as shown in FIG. 33. In this embodiment, the sleeve 25 includes a tubular body 326 that has a distraction extension 327 projecting from one side of one end of the sleeve. Unlike the sleeve 320, the sleeve 325 includes a separate outrigger spike 328 that is fixed to the tubular body by way of an engagement flange 329. It is understood that the outrigger spike 328 could be integrally formed with the tubular body 326 or connected to the body in some other fashion. Nevertheless, a primary feature of the sleeve 325 is that the spike 328 is disposed outside the diameter or outer wall of the tubular body 326. In this manner, the sleeve 325 and its hollow cannula opening can be offset further from the midline of the intervertebral disc space. Thus, interbody fusion devices, such as device 350, can be disposed farther outboard within that space using the sleeve 320.

In a further embodiment, a double-barrel sleeve 330 is provided. In this embodiment, two tubular bodies 331 and 332 are affixed at a joint 333. Each tubular body 331, 332 includes a respective distractor extension 334, 335. As with the other sleeve embodiments, the distractor extensions 334, 335 have a width that approximates the width of the distractor plug.

Figure 34:
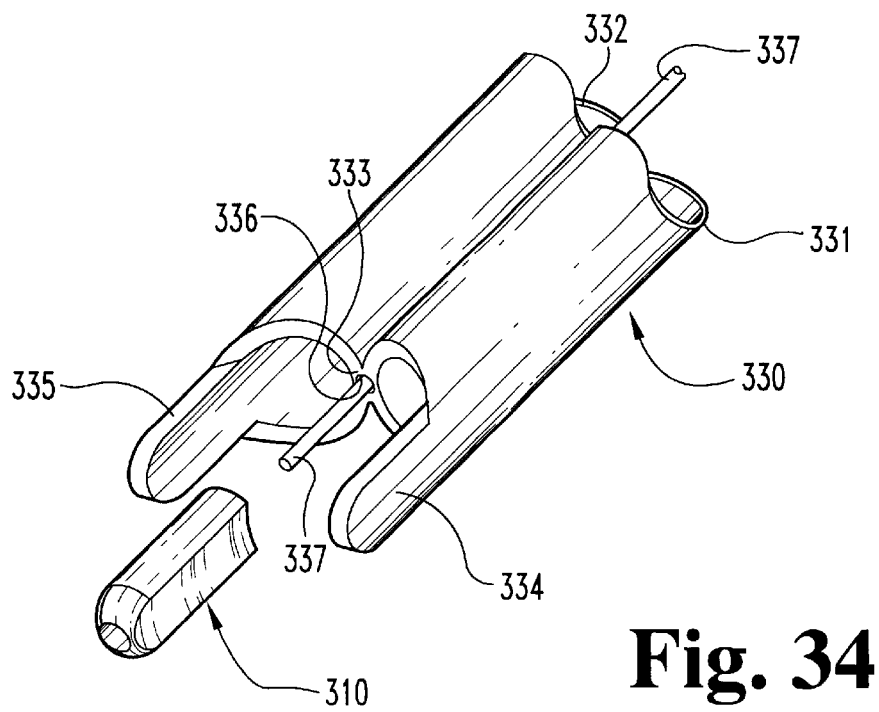
FIG. 34 is an end perspective view of a double barrel percutaneous surgical sleeve configured for engaging a distractor plug, such as the distractor plug shown in FIG. 29.

In this embodiment, a bore 336 is formed at the joint 333 between the two tubular bodies 331, 332. A spike, in the form of an elongated rod 337, is configured to extend through the bore 336. This spike can then engage a distractor plug, such as the distractor plug 310 shown in FIG. 34. With this double-barrel sleeve 330, there is no need to retract the sleeve, rotated to the bilateral position and re-dispose it within a distractor plug, as in the embodiment of FIG. 32. This double-barrel sleeve 330 provides an additional distractor extension, so that distraction is achieved not only at the midline location of the distractor plug 310, but also at the outboard positions of the distractor extensions 334, 335. Again, the distractor extensions are arranged together with the distractor plug so that various percutaneous operations can be occurring through the double-barrel sleeve of and in the intervertebral disc space.

One problem that faces many interbody fusion devices is the risk of backing out or retrograde expulsion of the device. In the case of push-in implants, the natural compressive forces achieved by the disc annulus in a distracted space can have a tendency to squeeze the fusion devices in a retrograde direction. These same forces, coupled with relative movement between the instrumented vertebrae, can also cause threaded fusion devices to slowly unthread. In accordance with the present invention, one embodiment of a fusion cage is provided that is designed to prevent this counter rotation of the fusion device. The fusion device 250 shown in FIG. 8 includes a pair of bone screws that are threaded into the adjacent vertebrae. These bone screws prevent the fusion device 250 from rotating within their prepared bores.

Figure 35:
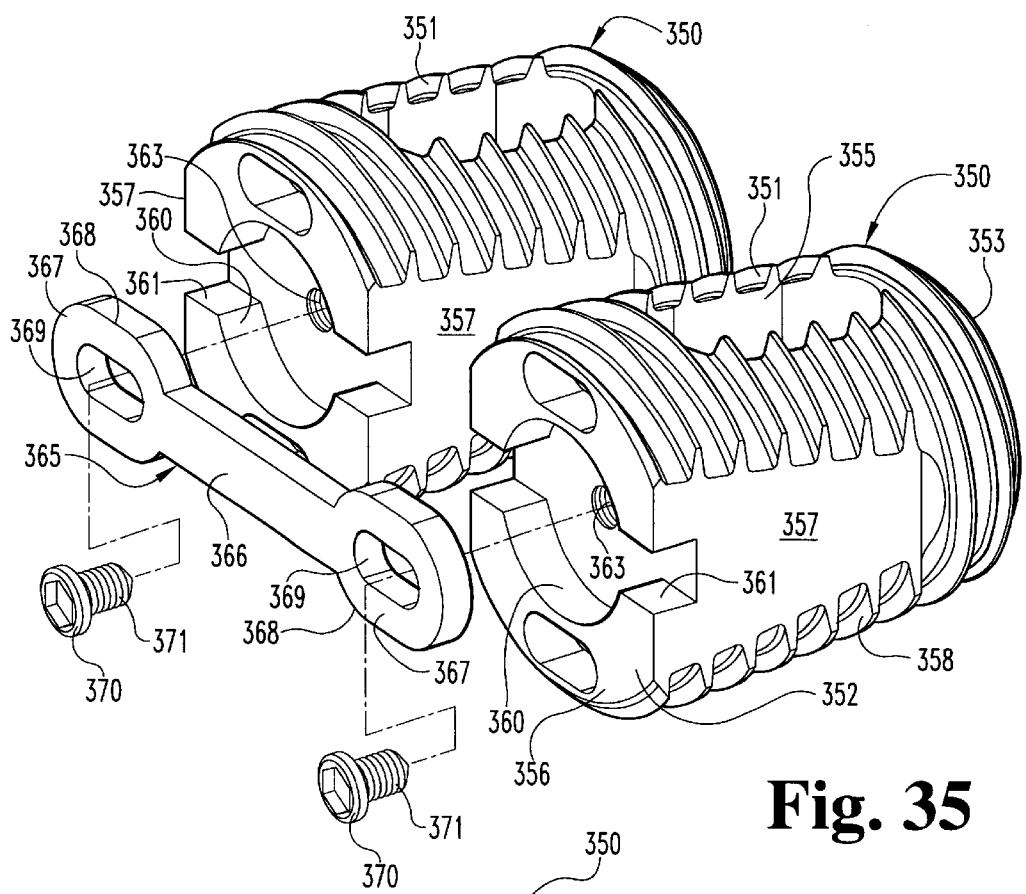
FIG. 35 is a side perspective view of an assembly in accordance with a further embodiment of the present invention utilizing a pair of fusion devices connected by a connector plate.
Figure 36:
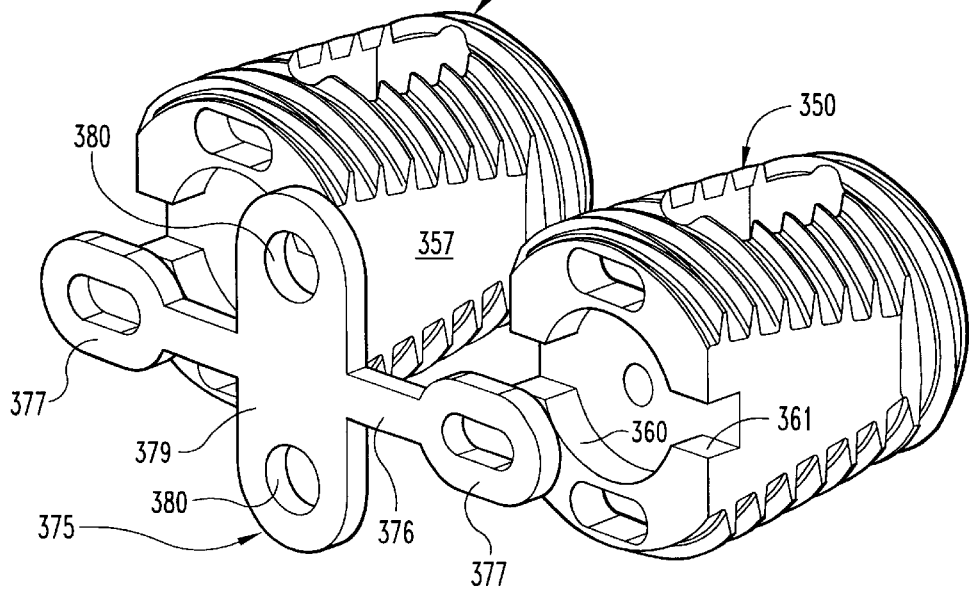
FIG. 36 is a side perspective view of an alternative embodiment of the assembly with a pair of fusion devices interconnected by an alternative connector plate.

Another approach is presented in FIGS. 35–36. In this approach, bilaterally placed fusion devices are connected laterally across the disc space, thereby preventing each device from rotating. In a first embodiment shown in FIG. 35, a pair of fusion devices 350 are provided that include a hollow body 351 having a first end 352 and a second end 353. As with the fusion devices previously discussed, the devices 350 each include a hollow interior 355 and an end wall 356. The devices also include external threads 358 that are adapted to be threaded into a prepared bore in adjacent vertebrae.

In a deviation from the previously discussed fusion devices, the fusion device 350 includes a recess 360 formed in the end wall 356. A lateral groove 361 traverses the recess 360 and opens at the flat side walls 357 of the device 350. Each device also includes a threaded bore 363 centrally formed at the base of the recess 360. When each fusion device 350 is placed bilaterally within an instrumented disc space, the devices are separated by some distance, as depicted in FIG. 35. This distance is spanned by a connector plate 365. The connector plate includes an elongate arm 366 having mating ends 367 formed at the ends of the arm. Each of the mating ends 367 defines an outer wall 368 that is generally configured to conform to the recesses 360 in each of the fusion devices 350. The elongate arm 366 is configured to rest within the groove 361 so that the connector plate 365 can span between and interconnect the two fusion devices 350.

The connector plate 365 is provided with a slot 369 at each of the mating ends 367. This slot is oriented directly above the threaded bore 363 in the end wall 356 of the fusion device 350. A locking screw 370 having a threaded stem 371 is provided that extends through each slot 369 and into the threaded bore 363. The locking screw 370 is then tightened into the bore to clamp the connector plate 365 to each of the interbody fusion devices 350. Thus, the presence of the connector plate 365 when disposed within the grooves 361 of the adjacent fusion devices, prevents each fusion device 350 from rotating when within the patient. The length of the connector plate 365 is dictated by the spacing of the fusion devices 350 within the disc space.

In an additional embodiment, a connector plate 375 is shown in FIG. 36. The connector plate includes an elongate arm 376 with mating ends 377, each element of which is similar to the like named elements of the connector plate 365. However, in an alternative configuration, the connector plate 375 includes an intermediate plate 379 that preferably projects perpendicularly outward from the elongate arm 376. The intermediate plate 379 is generally in the middle of the connector plate 375 and sized to sit between each of the fusion devices 350. In one specific embodiment, the intermediate plate 379 has a width that is sufficient so that the plate 379 is in contact with one side wall 357 of the adjacent devices 350.

In the illustrated embodiments, the focus has been on threaded fusion devices. However, it is understood that the present invention has utility in implanting non-threaded fusion devices, threaded and non-threaded spacers, and cylindrical or non-cylindrical devices or plugs.

In a further aspect of this embodiment, the intermediate plate 379 is provided with angled screw bores 380. In particular, these screw bores are angled so that a bone screw inserted through the bores can be driven upward into the vertebral endplates of the adjacent vertebrae. Preferably, the screw bores are oriented at an angle similar to the angle of the screw bores 268 of the fusion device 250. Thus, the connector plate 375 provides an additional degree of security to prevent retrograde expulsion of the interbody fusion device 350.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Laparoscopic instrumentation for performing surgical procedures between adjacent vertebrae, said instrumentation comprising:
   a tubular sleeve having a longitudinal axis and a hollow interior along said axis sized for advancement of surgical tools from outside the patient's body to the adjacent vertebrae, said sleeve including a spike connected with and projecting from said sleeve substantially parallel to said longitudinal axis; and
   a centering device including an elongated stem sized for introduction into the disc space between the adjacent vertebrae, said stem defining a bore sized to receive said spike of said tubular sleeve therethrough.

2. The laparoscopic instrumentation according to claim 1, wherein said bore is a keyed bore having a non-circular shape and said stem has a shape complementary to said keyed bore to prevent relative rotation between said sleeve and said centering device.

3. The laparoscopic instrumentation according to claim 1, wherein:
   said elongated stem of said centering device has a height sufficient to distract the disc space between the adjacent vertebrae; and
   said sleeve includes an extension projecting therefrom substantially parallel to said spike, said extension having a height substantially equal to the height of said elongated stem.

4. The laparoscopic instrumentation according to claim 1, wherein said sleeve includes a tubular wall and said spike extends contiguously from said wall.

5. The laparoscopic instrumentation according to claim 1, wherein said sleeve includes a tubular wall and said spike is attached to the outside of said wall.

6. The laparoscopic instrumentation according to claim 1 wherein: said sleeve includes a bore extending along the length of said sleeve; and said spike is sized for slidable passage through said bore in said sleeve.

7. The laparoscopic instrumentation according to claim 1, wherein said spike is integrally connected with said sleeve.

8. The laparoscopic instrumentation according to claim 1, wherein said spike is rigidly connected with said sleeve.

9. The laparoscopic instrumentation according to claim 1, wherein said spike is slidably connected with said sleeve.

10. The laparoscopic instrumentation according to claim 1, wherein said spike is non-rigidly connected with said sleeve.

11. The laparoscopic instrumentation according to claim 1, wherein said spike projects from an end wall of said sleeve.

12. The laparoscopic instrumentation according to claim 1, wherein said spike projects from a side wall of said sleeve.

13. Laparoscopic instrumentation for performing a surgical procedure between adjacent vertebrae, comprising:
   a plug adapted for introduction between the adjacent vertebrae; and
   a sleeve defining a hollow interior; and
   wherein one of said plug and said sleeve defines a passage, another of said plug and said sleeve defining a projection at least partially received within said passage to locate said sleeve relative to the adjacent vertebrae, said projection contiguously connected with and projecting from said another of said plug and said sleeve.

14. The laparoscopic instrumentation according to claim 13, wherein said plug defines said passage and said sleeve defines said projection.

15. The laparoscopic instrumentation according to claim 13, wherein said hollow interior of said sleeve extends along a longitudinal axis, said passage and said projection being arranged substantially parallel to said longitudinal axis.

16. The laparoscopic instrumentation according to claim 13, wherein said projection extends axially from a distal end of said sleeve.

17. The laparoscopic instrumentation according to claim 16, wherein said sleeve includes a side wall defining a bore, said bore extending from said distal end and sized to receive said projection therein.

18. The laparoscopic instrumentation according to claim 13, wherein said hollow interior of said sleeve is sized for advancement of one or more surgical devices from outside the patient's body to the adjacent vertebrae.

19. The laparoscopic instrumentation according to claim 18, wherein said sleeve has a tubular cross section, said plug having a curved side wall corresponding to said tubular cross section to provide clearance for said surgical devices during advancement through said sleeve.

20. The laparoscopic instrumentation according to claim 13, wherein said plug includes an outwardly extending flange having a bone engaging face for contacting at least one of the adjacent vertebrae when said plug is introduced between the adjacent vertebrae.

21. The laparoscopic instrumentation according to claim 13, wherein said plug includes opposite top and bottom bone engaging surfaces configured to resist expulsion of said plug from between the adjacent vertebrae.

22. The laparoscopic instrumentation according to claim 13, wherein said sleeve comprises a pair of tubular bodies, said tubular bodies having distal end portions affixed to one another at a central joint, said central joint defining one of said passage and said projection.

23. The laparoscopic instrumentation according to claim 22, wherein said plug has a height sufficient to distract a space between the adjacent vertebrae; and wherein each of said tubular bodies includes an extension member projecting therefrom having a height substantially equal to the height of said plug.

24. The laparoscopic instrumentation according to claim 13, wherein said projection is integrally connected with said another of said plug and said sleeve.

25. The laparoscopic instrumentation according to claim 13, wherein said projection is rigidly connected with said another of said plug and said sleeve.

26. The laparoscopic instrumentation according to claim 13, wherein said projection is slidably connected with said another of said plug and said sleeve.

27. The laparoscopic instrumentation according to claim 13, wherein said projection is non-rigidly connected with said another of said plug and said sleeve.

28. The laparoscopic instrumentation according to claim 13, wherein said projection extends contiguously from said another of said plug and said sleeve.

29. The laparoscopic instrumentation according to claim 13, wherein said projection projects from an end wall of said another of said plug and said sleeve.

30. Laparoscopic instrumentation for performing a surgical procedure between adjacent vertebrae, comprising:
   a plug adapted for introduction between the adjacent vertebrae; and
   a sleeve defining a hollow interior; and
   wherein one of said plug and said sleeve defines a passage, another of said plug and said sleeve defining a projection at least partially received within said passage to locate said sleeve relative to the adjacent vertebrae, at least a portion of said passage having a non-circular shape, said projection having a shaped portion substantially complementary to said non-circular shape of said passage to prevent relative rotation between said plug and said sleeve.

31. The laparoscopic instrumentation according to claim 30, wherein said at least a portion of said passage and said shaped portion of said projection have a square shape extension member is disposed said plug.

32. Laparoscopic instrumentation for performing a surgical procedure between adjacent vertebrae, comprising:
   a plug adapted for introduction between the adjacent vertebrae, said plug having a height sufficient to distract a space between the adjacent vertebrae; and
   a sleeve defining a hollow interior and including an extension member projecting therefrom having a height substantially equal to said height of said plug; and
   wherein one of said plug and said sleeve defines a passage, another of said plug and said sleeve defining a projection at least partially received within said passage to locate said sleeve relative to the adjacent vertebrae.

33. The laparoscopic instrumentation according to claim 32, wherein said extension member is disposed generally laterally opposite said plug relative to said sleeve.

34. Laparoscopic instrumentation for performing a surgical procedure between adjacent vertebrae, comprising:
   a plug adapted for introduction between the adjacent vertebrae; and
   a sleeve defining a hollow interior; and
   wherein said plug defines a passage, said sleeve defining a projection at least partially received within said passage to locate said sleeve relative to the adjacent vertebrae, said projection extending axially from a distal end of said sleeve and integrally formed with said sleeve.

35. Laparoscopic instrumentation for performing a surgical procedure between adjacent vertebrae, comprising:
   a plug adapted for introduction between the adjacent vertebrae; and
   a sleeve defining a hollow interior; and
   wherein one of said plug and said sleeve defines a passage, another of said plug and said sleeve defining a projection at least partially received within said passage to locate said sleeve relative to the adjacent vertebrae, said projection laterally coupled to an outer surface said sleeve.

36. A method for performing a surgical procedure between adjacent vertebrae, comprising:
   providing a plug;
   providing a sleeve defining a hollow interior, one of the plug and the sleeve defining a passage and another of the plug and the sleeve defining a projection;
   introducing the plug between the adjacent vertebrae; and
   inserting the projection within the passage to locate the sleeve relative to the adjacent vertebrae.

37. The method according to claim 36 further comprising advancing surgical instrumentation through the hollow interior of the sleeve from outside the patient's body toward the adjacent vertebrae.

38. The method according to claim 36, wherein the introducing includes distracting the disc space between the adjacent vertebrae.

39. The method according to claim 36, wherein the introducing includes centering the plug within the disc space between the adjacent vertebrae.

40. The method according to claim 36, further comprising:
   removing the projection from the passage;
   repositioning the sleeve relative to the plug; and
   reinserting the projection within the passage to locate the sleeve in a second position relative to the adjacent vertebrae.

41. The method according to claim 40, wherein the repositioning comprises rotating the sleeve to a laterally opposite position relative to the plug.

42. The method according to claim 36, further comprising advancing a surgical tool through the sleeve and performing a drilling operation on the adjacent vertebrae.

43. The method according to claim 36, further comprising advancing a surgical tool through the sleeve and performing a reaming operation on the adjacent vertebrae.

44. The method according to claim 36, further comprising advancing an implant through the sleeve and inserting the implant between the adjacent vertebrae.

* * * * *

UNITED STATES PATENT AND TRADEMARK OFFICE
CERTIFICATE OF CORRECTION

PATENT NO. : 6,695,851 B2
DATED : February 24, 2004
INVENTOR(S) : Zdeblick et al.

It is certified that error appears in the above-identified patent and that said Letters Patent is hereby corrected as shown below:

Column 25,
Line 47, replace "spike connected" with -- spike contiguously connected --.
Line 48, replace "from said" with -- from a portion of said --.

Column 26,
Line 34, replace "from said" with -- from a portion of said --.

Column 27,
Line 47, please delete "extension member is disposed said plug".
Line 59, replace "projection at" with -- projection contiguously connected with a portion thereof and at --.

Column 28,
Line 23, replace "surface said" with -- surface of said --.
Line 32, replace "projection within" with -- projection contiguously connected with a portion thereof within --.

Signed and Sealed this

Thirtieth Day of November, 2004

JON W. DUDAS
*Director of the United States Patent and Trademark Office*